(12) United States Patent
Gamero-Estevez et al.

(10) Patent No.: US 12,077,565 B2
(45) Date of Patent: Sep. 3, 2024

(54) CLAUDIN-TARGETING AGENTS AND USES THEREOF

(71) Applicants: Enrique Gamero-Estevez, Montreal (CA); Aimee Ryan, Montreal (CA); Makoto Nagano, Dorval (CA)

(72) Inventors: Enrique Gamero-Estevez, Montreal (CA); Aimee Ryan, Montreal (CA); Makoto Nagano, Dorval (CA)

(*) Notice: Subject to any disclaimer, the term of this patent is extended or adjusted under 35 U.S.C. 154(b) by 209 days.

(21) Appl. No.: 17/073,817

(22) Filed: Oct. 19, 2020

(65) Prior Publication Data

US 2021/0130418 A1 May 6, 2021

Related U.S. Application Data

(60) Provisional application No. 62/923,481, filed on Oct. 19, 2019.

(51) Int. Cl.
*C07K 14/33* (2006.01)

(52) U.S. Cl.
CPC .......... *C07K 14/33* (2013.01); *C07K 2319/21* (2013.01); *C07K 2319/23* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 2009/0202556 A1* | 8/2009 | Ohta | C07K 16/28 435/69.6 |
| 2015/0218644 A1* | 8/2015 | Santin | A61K 45/06 435/6.12 |

OTHER PUBLICATIONS

Shrestha et al. Anaerobe vol. 4, pp. 18-26, 2016. (Year: 2016).*
Of Fujita et al., Febs Letters, vol. 476, pp. 258-261. 2000. (Year: 2000).*
Ebihara et al. (The Journal of Pharmacology and Experimental Therapeutics vol. 316, No. 1, 2006). (Year: 2006).*

* cited by examiner

*Primary Examiner* — Jana A Hines
*Assistant Examiner* — Khatol S Shahnan Shah
(74) *Attorney, Agent, or Firm* — BCF LLP

(57) ABSTRACT

There are provided polypeptide constructs targeting claudin proteins that are useful for transiently disrupting tight junctions in a tissue. Pharmaceutical compositions and uses thereof in methods for enhancing delivery of therapeutic agents, for stem cell transplantation, and for treatment of male infertility are also provided.

12 Claims, 17 Drawing Sheets

Specification includes a Sequence Listing.

Structure:
- N-terminal domain (1-185): Cytotoxic activity
- C-terminal domain of C-CPE (185-319):
  - Claudin binding and stabilization domain.
  - Recognizes Cldn3, -4, -6, -7, -8 and -14.

His::NT::C-CPE::Cldn2EL2

```
                              SEQUENCE LISTING

<160> NUMBER OF SEQ ID NOS: 41

<210> SEQ ID NO 1
    <211> LENGTH: 285
    <212> TYPE: PRT
    <213> ORGANISM: Artificial Sequence
    <220> FEATURE:
    <223> OTHER INFORMATION: Polypeptide

<400> SEQUENCE: 1

Met Gly His His His His His His Met Ser His Thr Thr Pro Trp Thr
    1               5                   10                  15

Asn Pro Gly Leu Ala Glu Asn Phe Met Asn Ser Phe Met Gln Gly Leu
                    20                  25                  30

Ser Ser Met Pro Gly Phe Thr Ala Ser Gln Leu Asp Lys Met Ser Thr
                35                  40                  45

Ile Ala Gln Ser Met Val Gln Ser Ile Gln Ser Leu Ala Ala Gln Gly
            50                  55                  60

Arg Thr Ser Pro Asn Asp Leu Gln Ala Leu Asn Met Ala Phe Ala Ser
    65                  70                  75                  80

Ser Met Ala Glu Ile Ala Ala Ser Glu Glu Gly Gly Gly Ser Leu Ser
                    85                  90                  95

Thr Lys Thr Ser Ser Ile Ala Ser Ala Met Ser Asn Ala Phe Leu Gln
                    100                 105                 110

Thr Thr Gly Val Val Asn Gln Pro Phe Ile Asn Glu Ile Thr Gln Leu
                    115                 120                 125

Val Ser Met Phe Ala Gln Ala Gly Met Asn Asp Val Ser Ala Gly Thr
                130                 135                 140

Gly Glu Asn Leu Tyr Phe Gln Gly Arg Cys Val Leu Thr Val Pro Ser
    145                 150                 155                 160

Thr Asp Ile Glu Lys Glu Ile Leu Asp Leu Ala Ala Ala Thr Glu Arg
                    165                 170                 175

Leu Asn Leu Thr Asp Ala Leu Asn Ser Asn Pro Ala Gly Asn Leu Tyr
                    180                 185                 190

Asp Trp Arg Ser Ser Asn Ser Tyr Pro Trp Thr Gln Lys Leu Asn Leu
                    195                 200                 205

His Leu Thr Ile Thr Ala Thr Gly Gln Lys Tyr Arg Ile Leu Ala Ser
                    210                 215                 220

Lys Ile Val Asp Phe Asn Ile Tyr Ser Asn Asn Phe Asn Asn Leu Val
    225                 230                 235                 240

Lys Leu Glu Gln Ser Leu Gly Asp Gly Val Lys Asp His Tyr Val Asp
                    245                 250                 255

Ile Ser Thr Ala Trp Tyr Gly Asn Arg Ile Val Gln Glu Phe Tyr Asp
                    260                 265                 270

Pro Leu Thr Pro Ile Asn Ala Arg Tyr Glu Phe Gly Gln
                    275                 280                 285

<210> SEQ ID NO 2
    <211> LENGTH: 285
    <212> TYPE: PRT
    <213> ORGANISM: Artificial Sequence
    <220> FEATURE:
```

<223> OTHER INFORMATION: Polypeptide

<400> SEQUENCE: 2

```
Met Gly His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Thr
130                 135                 140

Gly Glu Asn Leu Tyr Phe Gln Gly Arg Cys Val Leu Thr Val Pro Ser
145                 150                 155                 160

Thr Asp Ile Glu Lys Glu Ile Leu Asp Leu Ala Ala Ala Thr Glu Arg
                165                 170                 175

Leu Asn Leu Thr Asp Ala Leu Asn Ser Asn Pro Ala Gly Asn Leu Tyr
            180                 185                 190

Asp Trp Arg Ser Ser Asn Ser Tyr Pro Trp Thr Gln Lys Leu Asn Leu
        195                 200                 205

His Leu Thr Ile Thr Ala Thr Gly Gln Lys Tyr Arg Ile Leu Ala Ser
210                 215                 220

Lys Ile Val Asp Phe Asn Ile Tyr Ser Asn Asn Phe Asn Asn Leu Val
225                 230                 235                 240

Lys Leu Glu Gln Ser Leu Gly Asp Gly Val Lys Asp His Tyr Val Asp
                245                 250                 255

Ile Ser Ser Ser Trp Asn Leu His Gly Ile Leu Arg Asp Phe Tyr Ser
            260                 265                 270

Pro Leu Val Pro Asp Ser Met Lys Phe Glu Ile Gly Glu
        275                 280                 285
```

<210> SEQ ID NO 3
<211> LENGTH: 280
<212> TYPE: PRT
<213> ORGANISM: Artificial Sequence
<220> FEATURE:
<223> OTHER INFORMATION: Polypeptide

<400> SEQUENCE: 3

```
Met Gly His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
50                  55                  60
```

Arg Thr Ser Pro Asn Asp Leu Gln Ala Leu Asn Met Ala Phe Ala Ser
 65                  70                  75                  80

Ser Met Ala Glu Ile Ala Ala Ser Glu Glu Gly Gly Gly Ser Leu Ser
                 85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Thr
        130                 135                 140

Gly Glu Asn Leu Tyr Phe Gln Gly Arg Cys Val Leu Thr Val Pro Ser
145                 150                 155                 160

Thr Asp Ile Glu Lys Glu Ile Leu Asp Leu Ala Ala Ala Thr Glu Arg
                165                 170                 175

Leu Asn Leu Thr Asp Ala Leu Asn Ser Asn Pro Ala Gly Asn Leu Tyr
            180                 185                 190

Asp Trp Arg Ser Ser Asn Ser Tyr Pro Trp Thr Gln Lys Leu Asn Leu
        195                 200                 205

His Leu Thr Ile Thr Ala Thr Gly Gln Lys Tyr Arg Ile Leu Ala Ser
210                 215                 220

Lys Ile Val Asp Phe Asn Ile Tyr Ser Asn Asn Phe Asn Asn Leu Val
225                 230                 235                 240

Lys Leu Glu Gln Ser Leu Gly Asp Gly Val Lys Asp His Tyr Val Asp
                245                 250                 255

Ile Ser Ser Ser Ile Ile Arg Asp Phe Tyr Asn Pro Leu Val Pro Glu
            260                 265                 270

Ala Gln Lys Arg Glu Met Gly Ala
        275                 280

<210> SEQ ID NO 4
<211> LENGTH: 274
<212> TYPE: PRT
<213> ORGANISM: Artificial Sequence
<220> FEATURE:
<223> OTHER INFORMATION: Polypeptide

<400> SEQUENCE: 4

Met Gly His His His His His His Met Ser His Thr Thr Pro Trp Thr
 1               5                  10                  15

Asn Pro Gly Leu Ala Glu Asn Phe Met Asn Ser Phe Met Gln Gly Leu
                 20                  25                  30

Ser Ser Met Pro Gly Phe Thr Ala Ser Gln Leu Asp Lys Met Ser Thr
            35                  40                  45

Ile Ala Gln Ser Met Val Gln Ser Ile Gln Ser Leu Ala Ala Gln Gly
        50                  55                  60

Arg Thr Ser Pro Asn Asp Leu Gln Ala Leu Asn Met Ala Phe Ala Ser
 65                  70                  75                  80

Ser Met Ala Glu Ile Ala Ala Ser Glu Glu Gly Gly Gly Ser Leu Ser
                 85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Thr
        130                 135                 140

Gly Glu Asn Leu Tyr Phe Gln Gly Arg Cys Val Leu Thr Val Pro Ser
145                 150                 155                 160

Thr Asp Ile Glu Lys Glu Ile Leu Asp Leu Ala Ala Ala Thr Glu Arg
            165                 170                 175

Leu Asn Leu Thr Asp Ala Leu Asn Ser Asn Pro Ala Gly Asn Leu Tyr
            180                 185                 190

Asp Trp Arg Ser Ser Asn Ser Tyr Pro Trp Thr Gln Lys Leu Asn Leu
            195                 200                 205

His Leu Thr Ile Thr Ala Thr Gly Gln Lys Tyr Arg Ile Leu Ala Ser
    210                 215                 220

Lys Ile Val Asp Phe Asn Ile Tyr Ser Asn Asn Phe Asn Asn Leu Val
225                 230                 235                 240

Lys Leu Glu Gln Ser Leu Gly Asp Gly Val Lys Asp His Tyr Val Asp
            245                 250                 255

Ile Ser Arg Glu Phe Tyr Asp Pro Thr Val Pro Val Ser Gln Lys Tyr
            260                 265                 270

Glu Leu

<210> SEQ ID NO 5
<211> LENGTH: 282
<212> TYPE: PRT
<213> ORGANISM: Artificial Sequence
<220> FEATURE:
<223> OTHER INFORMATION: Polypeptide

<400> SEQUENCE: 5

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
            35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Thr
    130                 135                 140

Gly Glu Asn Leu Tyr Phe Gln Gly Arg Cys Val Leu Thr Val Pro Ser
145                 150                 155                 160

Thr Asp Ile Glu Lys Glu Ile Leu Asp Leu Ala Ala Ala Thr Glu Arg
            165                 170                 175

Leu Asn Leu Thr Asp Ala Leu Asn Ser Asn Pro Ala Gly Asn Leu Tyr
            180                 185                 190

Asp Trp Arg Ser Ser Asn Ser Tyr Pro Trp Thr Gln Lys Leu Asn Leu
            195                 200                 205

His Leu Thr Ile Thr Ala Thr Gly Gln Lys Tyr Arg Ile Leu Ala Ser
    210                 215                 220

```
Lys Ile Val Asp Phe Asn Ile Tyr Ser Asn Asn Phe Asn Asn Leu Val
225                 230                 235                 240

Lys Leu Glu Gln Ser Leu Gly Asp Gly Val Lys Asp His Tyr Val Asp
            245                 250                 255

Ile Ser Ser Ile Ile Arg Asp Phe Tyr Asn Pro Leu Val Asp Val Ala
        260                 265                 270

Leu Lys Arg Glu Leu Gly Glu Ala Leu Tyr
        275                 280
```

<210> SEQ ID NO 6
<211> LENGTH: 274
<212> TYPE: PRT
<213> ORGANISM: Artificial Sequence
<220> FEATURE:
<223> OTHER INFORMATION: Polypeptide

<400> SEQUENCE: 6

```
Met Gly His His His His His Met Ser Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Thr
130                 135                 140

Gly Glu Asn Leu Tyr Phe Gln Gly Arg Cys Val Leu Thr Val Pro Ser
145                 150                 155                 160

Thr Asp Ile Glu Lys Glu Ile Leu Asp Leu Ala Ala Ala Thr Glu Arg
                165                 170                 175

Leu Asn Leu Thr Asp Ala Leu Asn Ser Asn Pro Ala Gly Asn Leu Tyr
            180                 185                 190

Asp Trp Arg Ser Ser Asn Ser Tyr Pro Trp Thr Gln Lys Leu Asn Leu
        195                 200                 205

His Leu Thr Ile Thr Ala Thr Gly Gln Lys Tyr Arg Ile Leu Ala Ser
210                 215                 220

Lys Ile Val Asp Phe Asn Ile Tyr Ser Asn Asn Phe Asn Asn Leu Val
225                 230                 235                 240

Lys Leu Glu Gln Ser Leu Gly Asp Gly Val Lys Asp His Tyr Val Asp
                245                 250                 255

Ile Ser Ser Ser His Arg Glu Ile Thr Ile Val Ser Phe Gly Tyr Ser
            260                 265                 270

Leu Tyr
```

<210> SEQ ID NO 7
<211> LENGTH: 27
<212> TYPE: PRT

```
<213> ORGANISM: Artificial Sequence
<220> FEATURE:
<223> OTHER INFORMATION: Polypeptide

<400> SEQUENCE: 7

Thr Ala Trp Tyr Gly Asn Arg Ile Val Gln Glu Phe Tyr Asp Pro Met
1               5                   10                  15

Thr Pro Val Asn Ala Arg Tyr Glu Phe Gly Gln
            20                  25

<210> SEQ ID NO 8
<211> LENGTH: 25
<212> TYPE: PRT
<213> ORGANISM: Artificial Sequence
<220> FEATURE:
<223> OTHER INFORMATION: Polypeptide

<400> SEQUENCE: 8

Trp Asn Leu His Gly Ile Leu Arg Asp Phe Tyr Ser Pro Leu Val Pro
1               5                   10                  15

Asp Ser Met Lys Phe Glu Ile Gly Glu
            20                  25

<210> SEQ ID NO 9
<211> LENGTH: 23
<212> TYPE: PRT
<213> ORGANISM: Artificial Sequence
<220> FEATURE:
<223> OTHER INFORMATION: Polypeptide

<400> SEQUENCE: 9

Trp Ser Ala Asn Thr Ile Ile Arg Asp Phe Tyr Asn Pro Val Val Pro
1               5                   10                  15

Glu Ala Gln Lys Arg Glu Met
            20

<210> SEQ ID NO 10
<211> LENGTH: 16
<212> TYPE: PRT
<213> ORGANISM: Artificial Sequence
<220> FEATURE:
<223> OTHER INFORMATION: Polypeptide

<400> SEQUENCE: 10

Val Arg Glu Phe Tyr Asp Pro Ser Val Pro Val Ser Gln Lys Tyr Glu
1               5                   10                  15

<210> SEQ ID NO 11
<211> LENGTH: 28
<212> TYPE: PRT
<213> ORGANISM: Artificial Sequence
<220> FEATURE:
<223> OTHER INFORMATION: Polypeptide

<400> SEQUENCE: 11

Trp Val Ala Asn Ala Ile Ile Arg Asp Phe Tyr Asn Ser Ile Val Asn
1               5                   10                  15

Val Ala Gln Lys Arg Glu Leu Gly Glu Ala Leu Tyr
            20                  25

<210> SEQ ID NO 12
<211> LENGTH: 14
<212> TYPE: PRT
<213> ORGANISM: Artificial Sequence
<220> FEATURE:
```

```
<223> OTHER INFORMATION: Polypeptide

<400> SEQUENCE: 12

Cys Ala His Arg Glu Thr Thr Ile Val Ser Phe Gly Tyr Ser
1               5                   10

<210> SEQ ID NO 13
<211> LENGTH: 131
<212> TYPE: PRT
<213> ORGANISM: Artificial Sequence
<220> FEATURE:
<223> OTHER INFORMATION: Polypeptide

<400> SEQUENCE: 13

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
                20                  25                  30

Gln Leu Asp Lys Met Ser Thr Ile Ala Gln Ser Met Val Gln Ser Ile
            35                  40                  45

Gln Ser Leu Ala Ala Gln Gly Arg Thr Ser Pro Asn Asp Leu Gln Ala
        50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val
        130

<210> SEQ ID NO 14
<211> LENGTH: 106
<212> TYPE: PRT
<213> ORGANISM: Artificial Sequence
<220> FEATURE:
<223> OTHER INFORMATION: Polypeptide

<400> SEQUENCE: 14

Arg Cys Val Leu Thr Val Pro Ser Thr Asp Ile Glu Lys Glu Ile Leu
1               5                   10                  15

Asp Leu Ala Ala Ala Thr Glu Arg Leu Asn Leu Thr Asp Ala Leu Asn
                20                  25                  30

Ser Asn Pro Ala Gly Asn Leu Tyr Asp Trp Arg Ser Ser Asn Ser Tyr
            35                  40                  45

Pro Trp Thr Gln Lys Leu Asn Leu His Leu Thr Ile Thr Ala Thr Gly
        50                  55                  60

Gln Lys Tyr Arg Ile Leu Ala Ser Lys Ile Val Asp Phe Asn Ile Tyr
65                  70                  75                  80

Ser Asn Asn Phe Asn Asn Leu Val Lys Leu Glu Gln Ser Leu Gly Asp
                85                  90                  95

Gly Val Lys Asp His Tyr Val Asp Ile Ser
            100                 105

<210> SEQ ID NO 15
<211> LENGTH: 27
<212> TYPE: PRT
```

```
<213> ORGANISM: Artificial Sequence
<220> FEATURE:
<223> OTHER INFORMATION: Polypeptide

<400> SEQUENCE: 15

Thr Ala Trp Tyr Gly Asn Arg Ile Val Gln Glu Phe Tyr Asp Pro Leu
1               5                   10                  15
Thr Pro Ile Asn Ala Arg Tyr Glu Phe Gly Gln
            20                  25

<210> SEQ ID NO 16
<211> LENGTH: 25
<212> TYPE: PRT
<213> ORGANISM: Artificial Sequence
<220> FEATURE:
<223> OTHER INFORMATION: Polypeptide

<400> SEQUENCE: 16

Trp Asn Leu His Gly Ile Leu Arg Asp Phe Tyr Ser Pro Leu Val Pro
1               5                   10                  15
Asp Ser Met Lys Phe Glu Ile Gly Glu
            20                  25

<210> SEQ ID NO 17
<211> LENGTH: 23
<212> TYPE: PRT
<213> ORGANISM: Artificial Sequence
<220> FEATURE:
<223> OTHER INFORMATION: Polypeptide

<400> SEQUENCE: 17

Trp Ser Ala Asn Thr Ile Ile Arg Asp Phe Tyr Asn Pro Leu Val Pro
1               5                   10                  15
Glu Ala Gln Lys Arg Glu Met
            20

<210> SEQ ID NO 18
<211> LENGTH: 16
<212> TYPE: PRT
<213> ORGANISM: Artificial Sequence
<220> FEATURE:
<223> OTHER INFORMATION: Polypeptide

<400> SEQUENCE: 18

Arg Glu Phe Tyr Asp Pro Thr Val Pro Val Ser Gln Lys Tyr Glu Leu
1               5                   10                  15

<210> SEQ ID NO 19
<211> LENGTH: 28
<212> TYPE: PRT
<213> ORGANISM: Artificial Sequence
<220> FEATURE:
<223> OTHER INFORMATION: Polypeptide

<400> SEQUENCE: 19

Trp Val Ala Asn Ser Ile Ile Arg Asp Phe Tyr Asn Pro Leu Val Asp
1               5                   10                  15
Val Ala Leu Lys Arg Glu Leu Gly Glu Ala Leu Tyr
            20                  25

<210> SEQ ID NO 20
<211> LENGTH: 14
<212> TYPE: PRT
<213> ORGANISM: Artificial Sequence
<220> FEATURE:
```

<223> OTHER INFORMATION: Polypeptide

<400> SEQUENCE: 20

Cys Ala His Arg Glu Ile Thr Ile Val Ser Phe Gly Tyr Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Polypeptide

<400> SEQUENCE: 21

Trp Thr Ala His Asn Val Ile Arg Asp Phe Tyr Asn Pro Met Val Ala
1               5                   10                  15

Ser Gly Gln Lys Arg Glu Met
            20

<210> SEQ ID NO 22
<211> LENGTH: 26
<212> TYPE: PRT
<213> ORGANISM: Artificial Sequence
<220> FEATURE:
<223> OTHER INFORMATION: Polypeptide

<400> SEQUENCE: 22

Trp Thr Ala His Ser Ile Ile Gln Asp Phe Tyr Asn Pro Leu Val Ala
1               5                   10                  15

Asp Ala Gln Lys Arg Glu Leu Gly Ala Ser
            20                  25

<210> SEQ ID NO 23
<211> LENGTH: 20
<212> TYPE: PRT
<213> ORGANISM: Artificial Sequence
<220> FEATURE:
<223> OTHER INFORMATION: Polypeptide

<400> SEQUENCE: 23

Gly His Gln Ile Val Thr Asp Phe Tyr Asn Pro Leu Thr Pro Met Asn
1               5                   10                  15

Val Lys Tyr Glu
            20

<210> SEQ ID NO 24
<211> LENGTH: 22
<212> TYPE: PRT
<213> ORGANISM: Artificial Sequence
<220> FEATURE:
<223> OTHER INFORMATION: Polypeptide

<400> SEQUENCE: 24

Trp Thr Ala His Ala Ile Ile Gln Asp Phe Tyr Asn Pro Leu Val Ala
1               5                   10                  15

Glu Ala Leu Lys Arg Glu
            20

<210> SEQ ID NO 25
<211> LENGTH: 24
<212> TYPE: PRT
<213> ORGANISM: Artificial Sequence
<220> FEATURE:
<223> OTHER INFORMATION: Polypeptide

```
<400> SEQUENCE: 25

Leu Tyr Ala Asn Lys Ile Thr Thr Glu Phe Phe Asp Pro Leu Tyr Met
1               5                   10                  15

Glu Gln Lys Tyr Glu Leu Gly Ala
            20

<210> SEQ ID NO 26
<211> LENGTH: 18
<212> TYPE: PRT
<213> ORGANISM: Artificial Sequence
<220> FEATURE:
<223> OTHER INFORMATION: Polypeptide

<400> SEQUENCE: 26

Tyr Asn Ser His Leu Asn Arg Lys Phe Glu Pro Val Phe Thr Phe Asp
1               5                   10                  15

Tyr Ala

<210> SEQ ID NO 27
<211> LENGTH: 26
<212> TYPE: PRT
<213> ORGANISM: Artificial Sequence
<220> FEATURE:
<223> OTHER INFORMATION: Polypeptide

<400> SEQUENCE: 27

Ser Trp Thr Thr Asn Asp Val Val Gln Asn Phe Tyr Asn Pro Leu Leu
1               5                   10                  15

Pro Ser Gly Met Lys Phe Glu Ile Gly Gln
            20                  25

<210> SEQ ID NO 28
<211> LENGTH: 19
<212> TYPE: PRT
<213> ORGANISM: Artificial Sequence
<220> FEATURE:
<223> OTHER INFORMATION: Polypeptide

<400> SEQUENCE: 28

Asn Ile Thr Thr Asp Phe Phe Asn Pro Leu Tyr Ala Gly Thr Lys Tyr
1               5                   10                  15

Glu Leu Gly

<210> SEQ ID NO 29
<211> LENGTH: 33
<212> TYPE: PRT
<213> ORGANISM: Artificial Sequence
<220> FEATURE:
<223> OTHER INFORMATION: Polypeptide

<400> SEQUENCE: 29

Trp Tyr Ala Val Asp Val Tyr Val Glu Arg Ser Ser Leu Val Leu His
1               5                   10                  15

Asn Ile Phe Leu Gly Ile Gln Tyr Lys Phe Gly Trp Ser Cys Trp Leu
            20                  25                  30

Gly

<210> SEQ ID NO 30
<211> LENGTH: 22
<212> TYPE: PRT
<213> ORGANISM: Artificial Sequence
<220> FEATURE:
<223> OTHER INFORMATION: Polypeptide
```

<400> SEQUENCE: 30

Trp Tyr Ala Thr Leu Val Thr Gln Glu Phe Phe Asn Pro Ser Thr Pro
1               5                   10                  15

Val Asn Ala Arg Tyr Glu
            20

<210> SEQ ID NO 31
<211> LENGTH: 22
<212> TYPE: PRT
<213> ORGANISM: Artificial Sequence
<220> FEATURE:
<223> OTHER INFORMATION: Polypeptide

<400> SEQUENCE: 31

Thr Ala His Asn Ile Ile Gln Asp Phe Tyr Asn Pro Leu Val Ala Ser
1               5                   10                  15

Gly Gln Lys Arg Glu Met
            20

<210> SEQ ID NO 32
<211> LENGTH: 23
<212> TYPE: PRT
<213> ORGANISM: Artificial Sequence
<220> FEATURE:
<223> OTHER INFORMATION: Polypeptide

<400> SEQUENCE: 32

Trp Thr Ala His Ala Ile Ile Arg Asp Phe Tyr Asn Pro Leu Val Ala
1               5                   10                  15

Glu Ala Gln Lys Arg Glu Leu
            20

<210> SEQ ID NO 33
<211> LENGTH: 22
<212> TYPE: PRT
<213> ORGANISM: Artificial Sequence
<220> FEATURE:
<223> OTHER INFORMATION: Polypeptide

<400> SEQUENCE: 33

Trp Tyr Gly His Gln Ile Val Thr Asp Phe Tyr Asn Pro Leu Ile Pro
1               5                   10                  15

Thr Asn Ile Lys Tyr Glu
            20

<210> SEQ ID NO 34
<211> LENGTH: 22
<212> TYPE: PRT
<213> ORGANISM: Artificial Sequence
<220> FEATURE:
<223> OTHER INFORMATION: Polypeptide

<400> SEQUENCE: 34

Trp Thr Ala His Ala Ile Ile Gln Asp Phe Tyr Asn Pro Leu Val Ala
1               5                   10                  15

Glu Ala Leu Lys Arg Glu
            20

<210> SEQ ID NO 35
<211> LENGTH: 24
<212> TYPE: PRT
<213> ORGANISM: Artificial Sequence
<220> FEATURE:

```
<223> OTHER INFORMATION: Polypeptide

<400> SEQUENCE: 35

Leu Tyr Ala Asn Lys Ile Thr Thr Glu Phe Phe Asp Pro Leu Phe Val
1               5                   10                  15

Glu Gln Lys Tyr Glu Leu Gly Ala
            20

<210> SEQ ID NO 36
<211> LENGTH: 18
<212> TYPE: PRT
<213> ORGANISM: Artificial Sequence
<220> FEATURE:
<223> OTHER INFORMATION: Polypeptide

<400> SEQUENCE: 36

Tyr Asn Ile His Leu Asn Lys Lys Phe Glu Pro Val Phe Ser Phe Asp
1               5                   10                  15

Tyr Ala

<210> SEQ ID NO 37
<211> LENGTH: 26
<212> TYPE: PRT
<213> ORGANISM: Artificial Sequence
<220> FEATURE:
<223> OTHER INFORMATION: Polypeptide

<400> SEQUENCE: 37

Ser Trp Thr Thr Asn Asp Val Val Gln Asn Phe Tyr Asn Pro Leu Leu
1               5                   10                  15

Pro Ser Gly Met Lys Phe Glu Ile Gly Gln
            20                  25

<210> SEQ ID NO 38
<211> LENGTH: 19
<212> TYPE: PRT
<213> ORGANISM: Artificial Sequence
<220> FEATURE:
<223> OTHER INFORMATION: Polypeptide

<400> SEQUENCE: 38

Asn Ile Thr Arg Asp Phe Phe Asp Pro Leu Tyr Pro Gly Thr Lys Tyr
1               5                   10                  15

Glu Leu Gly

<210> SEQ ID NO 39
<211> LENGTH: 33
<212> TYPE: PRT
<213> ORGANISM: Artificial Sequence
<220> FEATURE:
<223> OTHER INFORMATION: Polypeptide

<400> SEQUENCE: 39

Trp Tyr Ala Val Asp Val Tyr Val Glu Arg Ser Thr Leu Val Leu His
1               5                   10                  15

Asn Ile Phe Leu Gly Ile Gln Tyr Lys Phe Gly Trp Ser Cys Trp Leu
            20                  25                  30

Gly

<210> SEQ ID NO 40
<211> LENGTH: 22
<212> TYPE: PRT
<213> ORGANISM: Artificial Sequence
```

```
<220> FEATURE:
<223> OTHER INFORMATION: Polypeptide

<400> SEQUENCE: 40

Trp Tyr Ala Thr Leu Val Thr Gln Glu Phe Phe Asn Pro Ser Thr Pro
1               5                   10                  15

Val Asn Ala Arg Tyr Glu
            20

<210> SEQ ID NO 41
<211> LENGTH: 152
<212> TYPE: PRT
<213> ORGANISM: Artificial Sequence
<220> FEATURE:
<223> OTHER INFORMATION: Polypeptide

<400> SEQUENCE: 41

Met Gly His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Thr
    130                 135                 140

Gly Glu Asn Leu Tyr Phe Gln Gly
145                 150
```

CLAUDIN-TARGETING AGENTS AND USES THEREOF

CROSS-REFERENCE TO RELATED APPLICATIONS

The present application claims the benefit of priority from U.S. Provisional Application No. 62/923,481, filed Oct. 19, 2019, the entire contents of which are hereby incorporated by reference.

FIELD

The present disclosure relates to polypeptides targeting claudin proteins and uses thereof for transiently disrupting tight junctions in a tissue, compositions thereof, and methods of use thereof for enhancing delivery of therapeutic agents, for stem cell transplantation, and for treatment of male infertility.

BACKGROUND

Anti-cancer therapies target cells with high-turnover activity. As such, spermatogenesis is highly sensitive to the effects of chemo- and radio-therapy, which often leads to infertility in male oncology patients [1,2]. With increasing cancer survival rates [3,4], preservation and restoration of male fertility post-treatment has become a serious concern. Currently, the only option to preserve male fertility is sperm banking. However, this is not possible for childhood (i.e. pre-puberty) cancer patients who do not produce sperm at the time of therapy. This illustrates a critical need for a strategy to preserve fertility in this vulnerable population.

One of the ways through which anti-cancer therapies impair spermatogenesis, causing male infertility, is by inducing the loss of spermatogonial stem cells (SSCs). These SSCs are critical for spermatogenesis, as they self-renew throughout life and continuously give rise to daughter germ cells that are committed to differentiation into sperm [5]. Although childhood cancer patients do not produce sperm at the time of therapy, SSCs are present from birth and persist throughout life. Thus, the cryopreservation of SSCs before anti-cancer therapy, and their transplantation back into a patient afterwards, may provide a strategy to safeguard fertility for "men of any age" whose reproductive ability is at risk.

Spermatogenesis is a complex process that is regulated by interactions with Sertoli cells, which are the sole somatic cell type in the seminiferous epithelium [6,7]. The process of spermatogenesis can be divided into three phases [8]. Firstly, in the proliferation phase, SSCs located in the SSC niche, on the basal membrane of the seminiferous epithelium, self-renew and produce more committed spermatogonia that mitotically differentiate to increase their population size. In the second phase, differentiated spermatogonia leave the basal membrane and move towards the lumen, while undergoing meiosis to generate haploid spermatids. In the third phase, spermatids transform into spermatozoa. However, for cryopreserved SSCs transplanted post-treatment to effectively regenerate spermatogenesis, these SSCs must migrate to the basal membrane, survive, and repopulate the SSC niche in a process referred to as SSC-engraftment.

For SSC engraftment to occur, SSCs must traverse the tight junctions formed between Sertoli cells, which constitute the blood-testis-barrier (BTB). The BTB divides the seminiferous epithelium into two compartments: (1) the basal compartment, containing spermatogonia and (2) the adluminal compartment, containing spermatocytes, spermatids and spermatozoa. This physical separation between the basal and adluminal compartments ensures the maintenance of the distinct microenvironments required for the different steps in germ cell development. The BTB protects meiotic and haploid cells from potentially harmful substances by limiting their diffusion from the blood and the interstitial space. This barrier also protects haploid spermatids that express 'foreign' proteins from immunological attack [9].

Although the BTB represents an important protective barrier, it is also the greatest obstacle for SSC engraftment. Consistent with this, we have previously shown that SSC engraftment efficiency in mice is 12% [10, 11]; i.e., only 1 out of 8 transplanted SSCs actually engraft and regenerate spermatogenesis. The ability of the BTB to impede SSC engraftment after transplantation has been demonstrated using recipient mice of different ages [12]. In mice, the BTB is established 12-14 days after birth [13]. Accordingly, 8- to 10-fold more transplanted SSCs engraft in recipient testes of 5- to 12-day-old pups who lack a BTB, relative to adult recipient testes [12]. Interestingly, engraftment-defective SSCs that are unable to engraft in adult testes after transplantation were able to do so in pup testes that have not established BTBs [14]. These results demonstrate that the BTB acts as an obstacle for SSC engraftment, suggesting that opening the BTB in adult mice may improve SSC engraftment.

Opening the BTB to improve SSC engraftment may be possible by targeting the major components of the BTB, which include occludin and claudins (Cldns). Although occludin and Cldns are structurally similar, they have no sequence homology; moreover, occludin is undetectable in human testes [15], whereas Cldns are found on the BTB in both mice and humans. Claudins have two extracellular loops (EL1 and EL2) and two intracellular termini [16]. EL1 determines the size and charge selectivity of the barrier and EL2 interacts with claudin molecules on adjacent cells [17]. Individual claudin family members contribute specific attributes with respect to the paracellular barrier properties of the tight junctions. Although many claudin family members are expressed in mouse testes [9,12,14], Cldn1, 3, 5, and 11 are the best studied with respect to their protein expression and functions.

Of notable interest, Cldn11 is first detectable in the testis coincident with BTB establishment (P15 and P13, respectively) and is expressed throughout the seminiferous tubules. Moreover, Cldn11-null mice lack Sertoli cell tight junctions and do not form the BTB [18]. Although meiotic and haploid germ cells emerge in Cldn11-null mice, these cells cannot be appropriately segregated in the seminiferous epithelium and die. Consequently, Cldn11-null males lack spermatogenesis and are sterile. These studies reveal the importance of Cldn11 in BTB formation and maintenance of spermatogenesis.

Claudins are a large family of proteins found in tight junctions throughout the body. There are more than 30 claudin family members with unique and overlapping functions. Claudins display tissue-specific and spatially-restricted expression and their function is highly context-specific. Tight junction barrier properties are determined by the specific combination of claudins present, suggesting that modifying claudin expression could potentially provide clinically relevant function.

There is a need for treatments to restore and preserve male fertility after toxic therapies such as anti-cancer therapies and for treatments that can transiently disrupt tight junctions

SUMMARY

It is an object of the present invention to ameliorate at least some of the deficiencies present in the prior art. Embodiments of the present technology have been developed based on the inventors' appreciation that reversibly removing claudins from the cell membrane could transiently disrupt the tight junctions, and thereby increase cellular transplantation efficiency and enhance delivery of therapeutic agents. Such methods can have a wide range of clinical use, such as, for example and without limitation, restoration of male fertility by increasing SSC transplantation efficiency.

In a first broad aspect, there are provided polypeptide constructs that target claudin proteins at tight junctions. Polypeptide constructs comprise: a first region comprising a C-terminal domain of *Clostridium perfringens* enterotoxin (C-CPE) with the claudin-binding domain removed; and a second region comprising the second extracellular loop (EL2) of a claudin protein. The polypeptide can be designed to target a specific claudin protein of interest based on the EL2 region chosen: for example, the claudin11 EL2 will bind and target claudin 11 specifically; claudin3 EL2 will bind and target claudin3 specifically; and so on. In this way, specific claudins, and specific tight junctions where the selected claudins are expressed, can be targeted in the body.

The C-CPE region represents the C-terminal domain of *Clostridium perfringens* enterotoxin in which the toxin at the N-terminal has been removed. The claudin-binding domain is removed to avoid targeting undesired claudins. The C-CPE generally acts as a stabilization domain to stabilize the claudin EL2 region in the polypeptide construct. Specificity of claudin targeting is provided by the claudin EL2 region linked to the C-CPE region, which binds to the claudin in the tight junction leading to its removal from the cell surface. Without wishing to be limited by theory, it is believed the polypeptide acts at the cell surface to bind to the extracellular domain of the targeted claudin and remove it from the cell membrane. The complex of the polypeptide and the claudin are internalized and targeted for degradation. This process is non-toxic to the cell. This abrogates claudin-claudin interactions between adjacent cells and opens the paracellular space between cells. The removal of the targeted claudin is reversible and transient; once the polypeptide construct has been degraded, washed away, or otherwise removed, the claudins at the cell surface will be replaced by the cells and the tight junction is restored accordingly. Thus, polypeptide constructs provided herein can be used to transiently disrupt tight junctions.

In some embodiments, the C-CPE region in the polypeptide construct comprises amino acids 186 to 290 of *Clostridium perfringens* enterotoxin. In some embodiments, the C-CPE region in the polypeptide construct has the amino acid sequence set forth in SEQ ID NO: 14, or a functionally equivalent sequence having at least 80%, at least 90%, at least 95%, at least 98%, or at least 99% identity thereto.

The polypeptide construct may comprise the EL2 region of any claudin which is targeted. In some embodiments, the EL2 region is from claudin 1, 2, 3, 4, 5, 6, 7, 8, 9, 10, 11, 12, 14, 15, 16 or 19. In some embodiments, the EL2 region is from claudin 1, 2, 3, 5, 8 or 11. In one embodiment, the EL2 region is from claudin 11. The portion of the claudin EL2 region used is not particularly limited, so long as it specifically binds and removes the targeted claudin in the tight junction. For example, it may include the entire EL2 region, or a claudin-binding fragment or portion thereof. In some embodiments, the EL2 region comprises the amino acid sequence set forth in any one of SEQ ID Nos: 7-12 and 15-40, or a functionally equivalent sequence having at least 80%, at least 90%, at least 95%, at least 98%, or at least 99% identity thereto.

In some embodiments, the claudin-targeting polypeptide constructs further comprise one or more tag region. The tag region may comprise a detectable tag, such as a His tag; a tag for purification, such as a His tag (e.g., $His_6$) or a GST tag; and/or a tag for increasing solubility of the polypeptide such as the N-terminal domain from Euprosthenops australis major ampullate spidroin 1 (NT). In some embodiments, the polypeptide construct further comprises a TEV protease recognition sequence. In some embodiments, the polypeptide construct further comprises the amino acid sequence set forth in any one of SEQ ID Nos: 13 and 41, or a functionally equivalent sequence having at least 80%, at least 90%, at least 95%, at least 98%, or at least 99% identity thereto.

In some embodiments, there are provided nucleic acid molecules encoding the polypeptide constructs provided herein. Expression vectors comprising the nucleic acid molecules and/or encoding the polypeptide constructs of the present technology are also provided. In an embodiment, a cellular host comprising the nucleic acid or the vector is provided.

In a second broad aspect, there are provided pharmaceutical compositions comprising a polypeptide construct provided herein, and a pharmaceutically acceptable carrier, diluent or excipient.

In another broad aspect, there are provided methods for transiently disrupting tight junctions in a tissue in a subject. Such methods comprise administering an effective amount of the polypeptide construct or pharmaceutical composition provided herein to the subject, wherein the polypeptide construct targets one or more claudin protein in the tight junction such that the tight junction is disrupted. The tissue in which the tight junctions are disrupted may be any epithelial or endothelial tissue for which disruption of a paracellular barrier is desired. Non-limiting examples include the blood-brain-barrier (BBB), the blood-testis-barrier (BTB), the intestinal barrier, and barriers in the kidney (nephronic barriers).

In another aspect, there are provided methods for delivery of a therapeutic agent to a subject, comprising administering the therapeutic agent in combination with an effective amount of the polypeptide construct or pharmaceutical composition provided herein, wherein the polypeptide construct targets one or more claudin protein in a tissue of the subject and thereby disrupts tight junctions in the tissue, such that delivery of the therapeutic agent is improved as compared to administration of the therapeutic agent without the polypeptide construct. The therapeutic agent is not particularly limited and may be, for example and without limitation, a low molecular weight compound (e.g., a drug), a polypeptide, an antibody, a cell such as a stem cell, a gene delivery vector, and the like. The tissue in which the tight junctions are disrupted may be any epithelial or endothelial tissue for which disruption of a paracellular barrier is desired. Non-limiting examples include the blood-brain-barrier (BBB), the blood-testis-barrier (BTB), the intestinal barrier, and barriers in the kidney (nephronic barriers).

In another aspect, there are provided methods of increasing cellular transplantation efficiency, e.g., stem cell transplantation, comprising administering an effective amount of the polypeptide construct or pharmaceutical composition provided herein to the subject in combination with cellular transplantation, such that tight junctions are transiently disrupted and cellular transplantation (e.g., stem cell engraftment) is improved as compared to transplantation without the polypeptide construct. In an embodiment, a method of increasing efficiency or engraftment of spermatogonial stem cell (SSC) transplantation in the testes is provided.

In another broad aspect, there are provided methods of treating infertility in a male mammal in need thereof, comprising administering an effective amount of the polypeptide construct or pharmaceutical composition provided herein to the male mammal in combination with transplantation of spermatogonial stem cells (SSCs) in the testes. In some embodiments, the polypeptide construct or the pharmaceutical composition is injected into the interstitium of the testes and/or the seminiferous tubules of the testes. In an embodiment, the male mammal is a human cancer patient who has been treated with an anti-cancer therapy such as a chemotherapeutic agent or subjected to irradiation. In an embodiment, the spermatogonial stem cells are autologous stem cells isolated from the patient before said treatment with the anti-cancer therapy.

It should be understood that, in methods provided herein, the polypeptide construct or pharmaceutical composition may be administered to the subject before, during (at the same time as), or after the therapeutic agent, e.g., transplantation of cells. In some embodiments, the polypeptide construct or pharmaceutical composition is administered before administration of the therapeutic agent, e.g., before stem cell transplantation. In some embodiments, the polypeptide construct or pharmaceutical composition is administered after administration of the therapeutic agent, e.g., after stem cell transplantation. In some embodiments, the polypeptide construct or pharmaceutical composition is administered at the same time as administration of the therapeutic agent, e.g., concomitantly with stem cell transplantation. In such methods, the polypeptide construct and the therapeutic agent, e.g., stem cells, may be formulated separately and administered in separate compositions, or may be formulated together in one composition, depending on the particular condition being treated and the nature of the therapeutic agent.

In an embodiment, the polypeptide construct provided herein is capable of increasing SSC transplantation efficiency by reducing expression of Cldn11 at the BTB tight junctions (removing Cldn11 from the tight junctions), thereby disrupting the BTB. In this way the polypeptide construct can improve SSC transplantation efficiency, in order to restore fertility. The removal of the Cldn11 is transient, so that the BTB will be restored after the polypeptide construct is removed (e.g., degraded, washed away).

In a further aspect, there are provided kits for transiently disrupting a tight junction in a tissue in a subject in need thereof, comprising a polypeptide construct (or a pharmaceutical composition thereof), as described herein; optionally one or more additional component such as acids, bases, buffering agents, inorganic salts, solvents, antioxidants, preservatives, or metal chelators; and instructions for use thereof. Kits may also comprise a nucleic acid or a vector for expression of a polypeptide construct, and instructions for expression and purification of the polypeptide construct.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to embodiments of the present invention, and in which:

Figure 12:
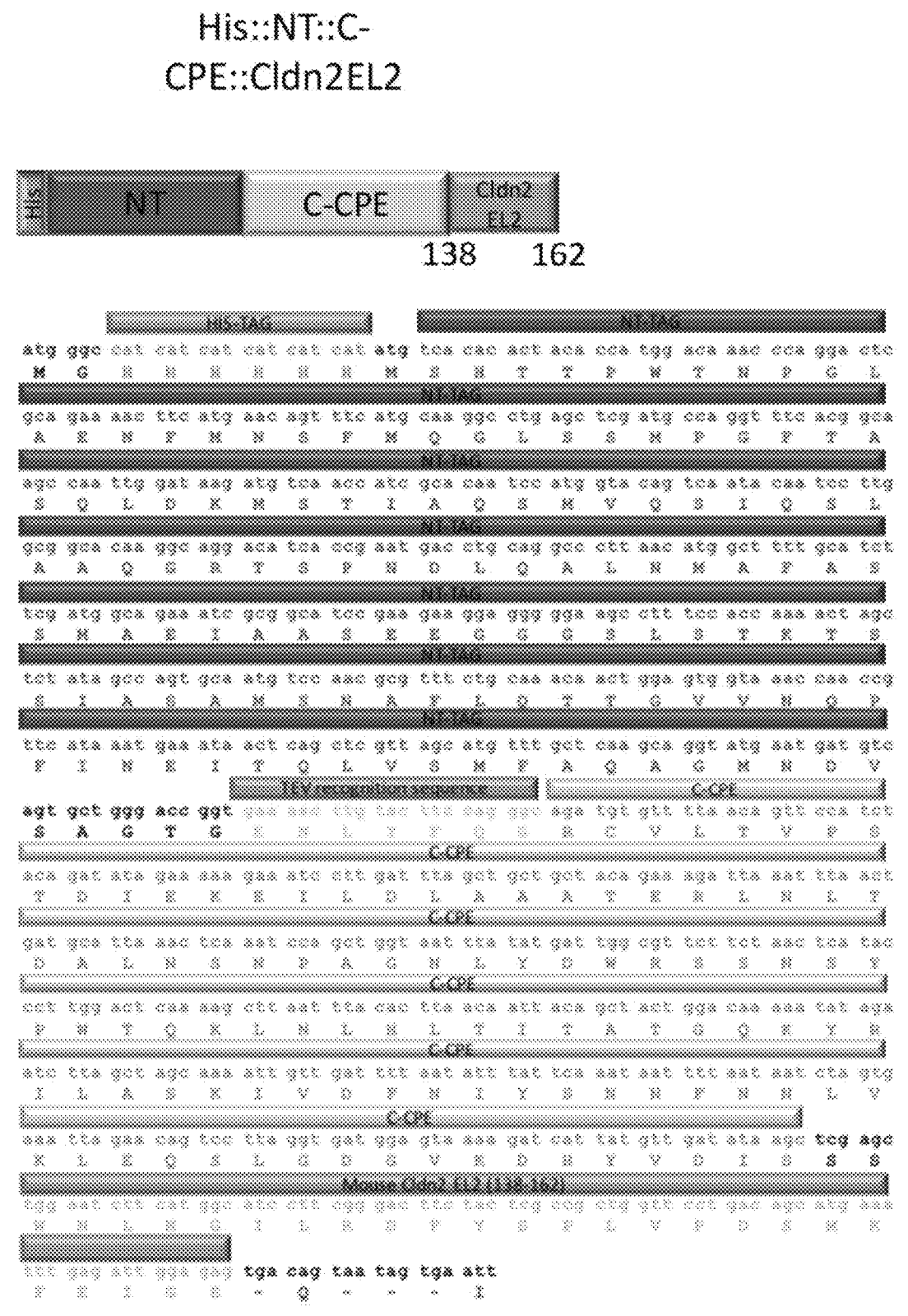

FIG. 12 shows the nucleotide and amino acid sequence of the His::NT::C-CPE::Cldn2EL2 polypeptide, in accordance with certain embodiments, which has been color-coded to differentiate the various domains as follows: His-tag is shown in blue; solubility tag is shown in purple; TEV recognition sequence is shown in orange; C-CPE region is shown in grey; and claudin EL2 domain is shown in green.

Figure 13:
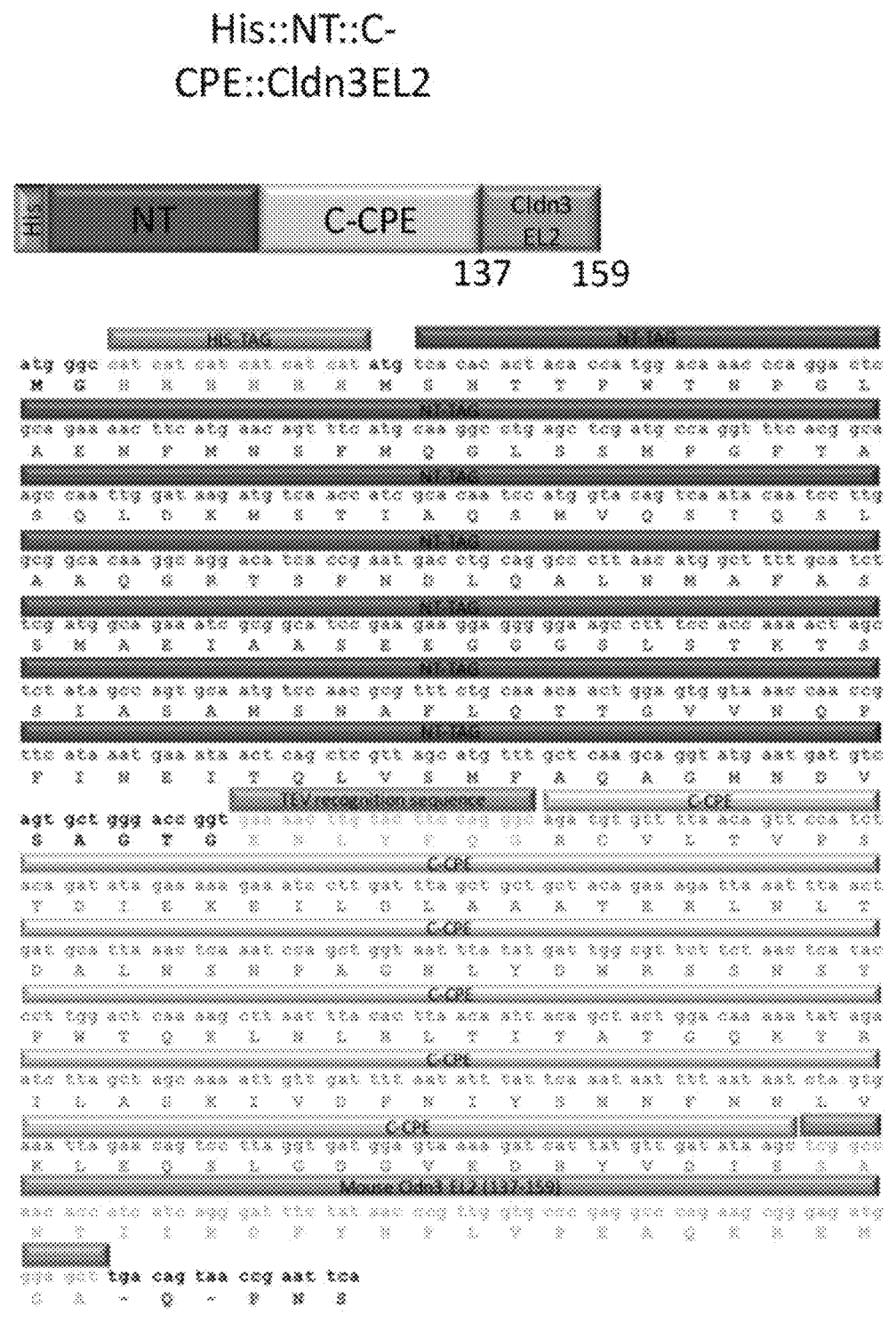

FIG. 13 shows the nucleotide and amino acid sequence of the His::NT::C-CPE::Cldn3EL2 polypeptide, in accordance with certain embodiments, which has been color-coded to differentiate the various domains as follows: His-tag is shown in blue; solubility tag is shown in purple; TEV recognition sequence is shown in orange; C-CPE region is shown in grey; and claudin EL2 domain is shown in green.

Figure 14:
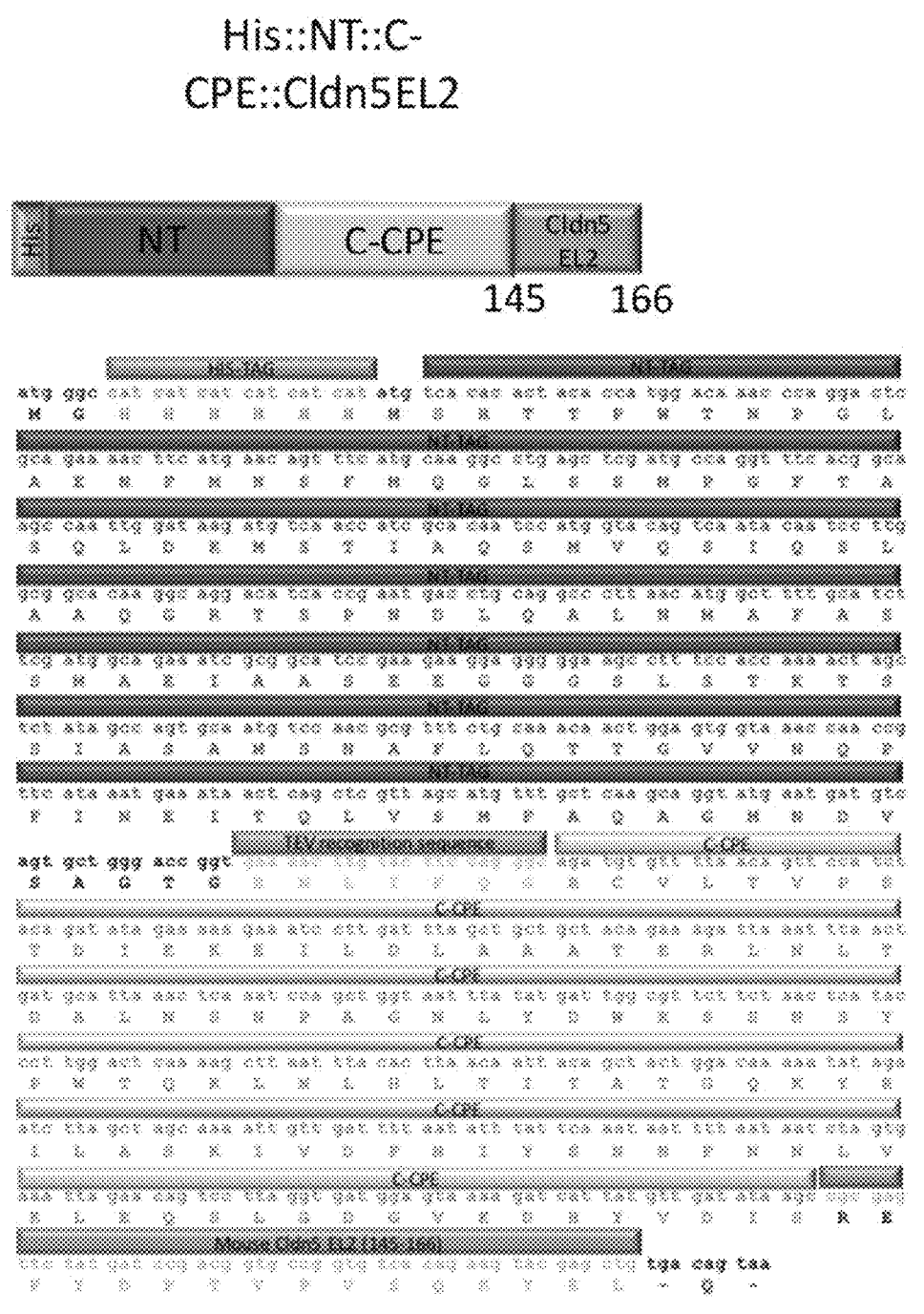

FIG. 14 shows the nucleotide and amino acid sequence of the His::NT::C-CPE::Cldn5EL2 polypeptide, in accordance with certain embodiments, which has been color-coded to differentiate the various domains as follows: His-tag is shown in blue; solubility tag is shown in purple; TEV recognition sequence is shown in orange; C-CPE region is shown in grey; and claudin EL2 domain is shown in green.

DETAILED DESCRIPTION

Figure 1:
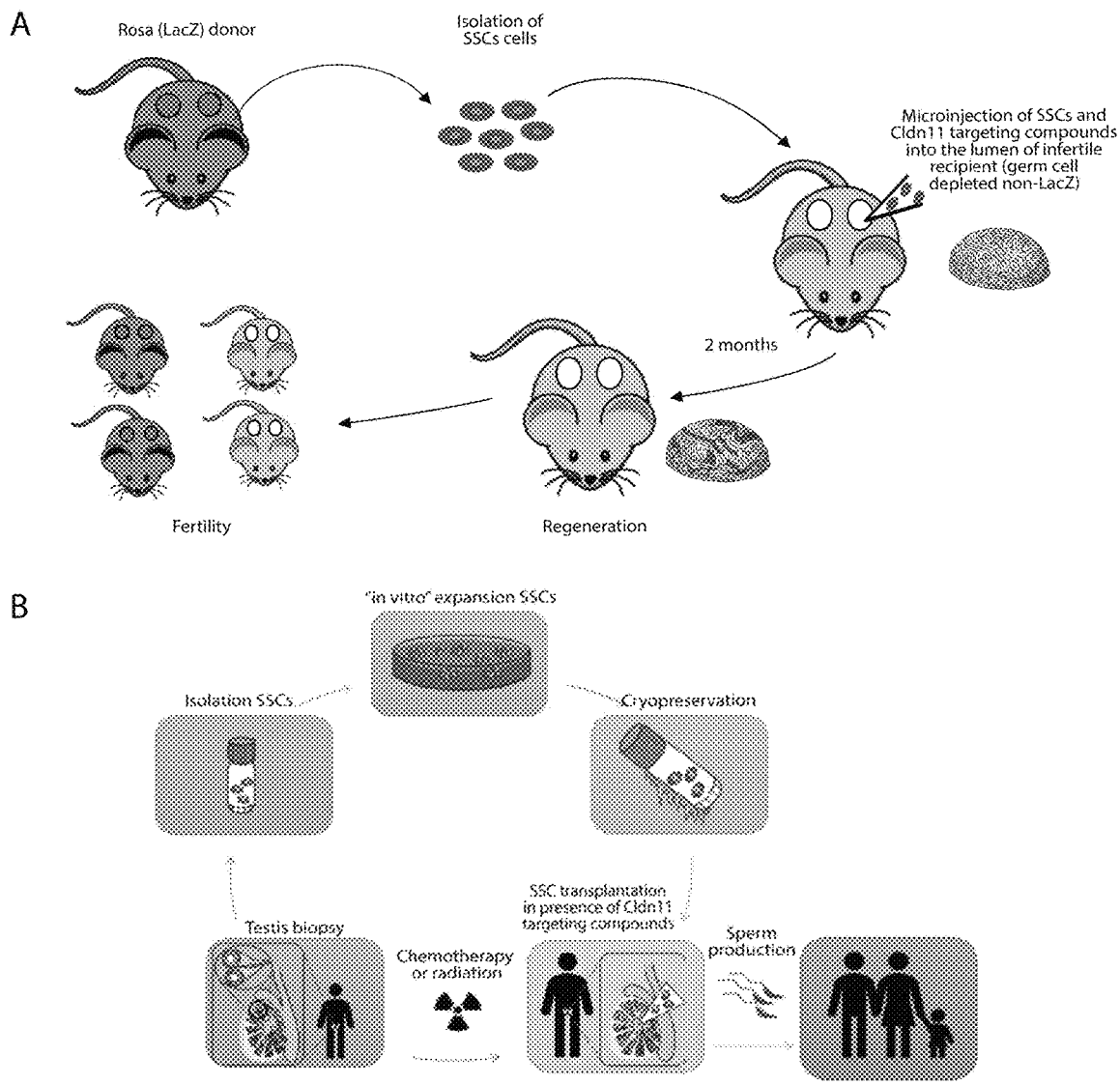
FIG. 1 is a schematic diagram showing a method in accordance with certain embodiments for SSC transplantation and use of a polypeptide construct for the restoration of fertility following SSC transplantation in (A) male mice and (B) male humans who have been treated with anti-cancer therapy. (C) shows a representative claudin protein at the cell surface. (D) shows a schematic drawing of a CPE protein.
Figure 1C:
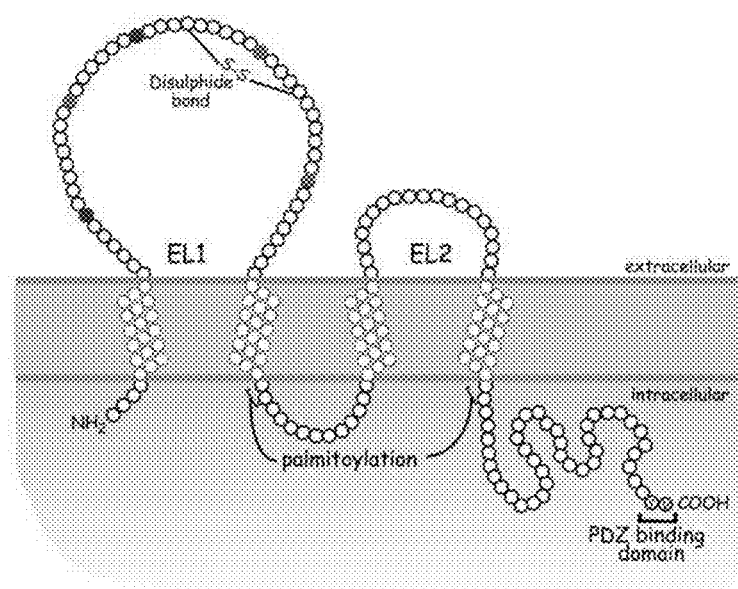
Figure 1D:
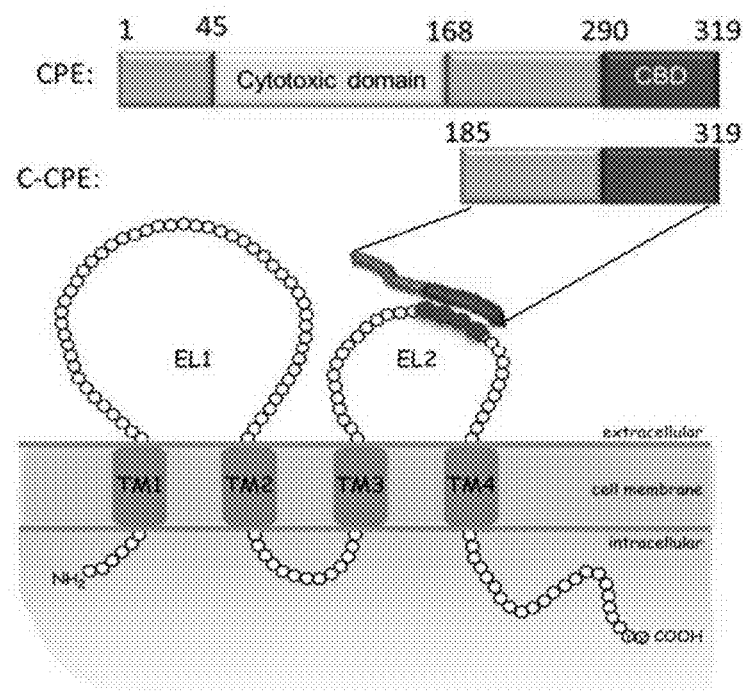
Figure 2:
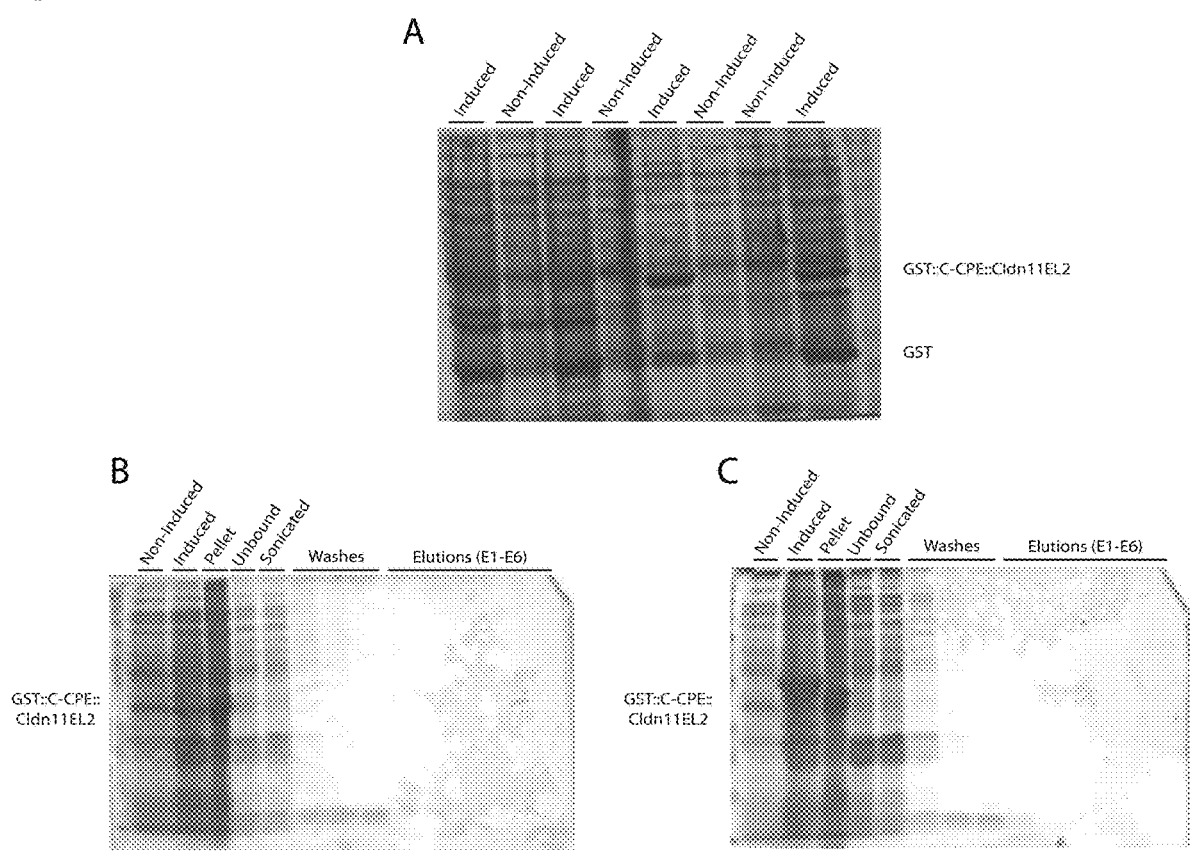
FIG. 2 shows the electrophoresis analysis of the insoluble protein purification fractions, (resulting from the GST::C-CPE::Cldn11EL2 constructs). (A) Induced (using 0.4 mM of IPTG) and non-induced samples from 4 independent cultures indicate that GST::C-CPE::Cldn11EL2 expression is visibly induced by IPTG. (B) Samples of GST::C-CPE::Cldn11EL2 constructs using C-CPE sequence 186-303aa were purified. They showed no visible evidence of protein in the soluble elution fraction. (C) Samples of GST::C-CPE::Cldn11EL2 constructs using C-CPE sequence 186-290aa were purified. They showed no visible evidence of protein in the soluble elution fraction.
Figure 3:
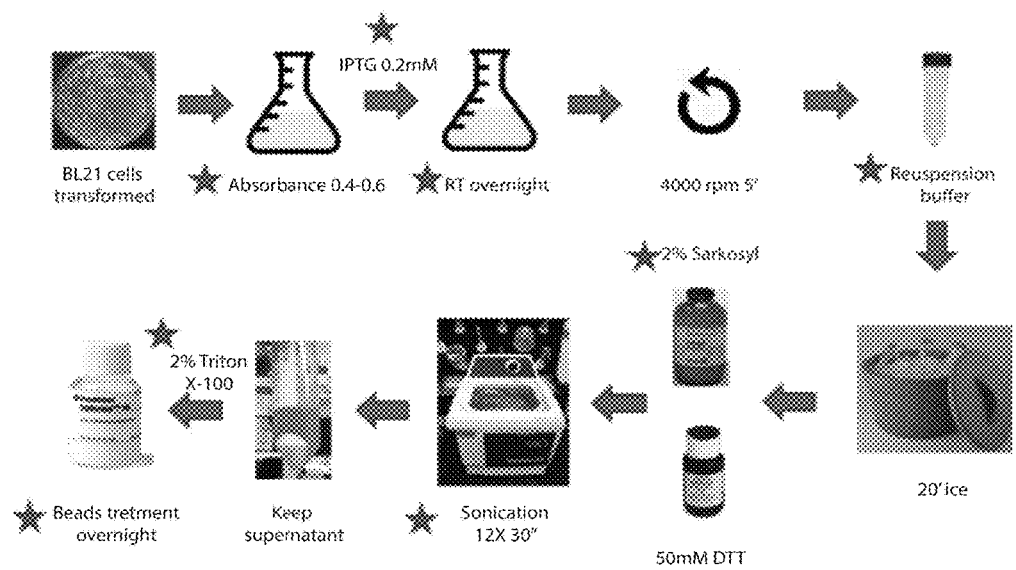
FIG. 3 is a schematic diagram showing the steps involved in the protein purification process to generate a soluble Cldn11-targeting protein. Each step marked by a 'star' reflects a step that required troubleshooting.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "functionally equivalent" is used herein to refer to a protein sequence that has the same or substantially the same biological activity or function as the original sequence from which it is derived. For example, a fragment or variant polypeptide that maintains the same or substantially the same claudin targeting, claudin binding and/or claudin removing activity as the original sequence would be considered functionally equivalent herein.

The term "Spermatogonial stem cells (SSCs)" as used herein refers to stem cells that maintain spermatogenesis (sperm producing process) and male fertility throughout their life. These cells continuously self-renew and give rise to daughter germ cells that are committed to differentiating into sperm [5]. SSCs are functionally defined by their capacity to regenerate and give rise to cells that differentiate into sperm; SSCs cannot be defined by biochemical or immunological markers at present.

As used herein, the term "Blood-testis-barrier (BTB)" refers to the tight junctions formed between Sertoli cells in the epithelium of the seminiferous tubule. The protein Zona Occludens 1 (ZO-1) serves as a marker of these tight junctions and thus the BTB.

As used herein, the term "SSC engraftment" refers to the process whereby transplanted SSCs migrate to the basal membrane, survive, and repopulate the SSC niche within the seminiferous tubule As used herein, the term "SSC transplantation efficiency" refers to the success rate of SSC engraftment in the SSC niche following SSC transplantation As used herein, the term "SSC niche" refers to the location on the basal membrane of the seminiferous epithelium where SSCs self-renew and produce more committed spermatogonia for sperm generation.

As used herein, the term "tight junctions" refers to a facet of the BTB formed by neighboring Sertoli cells, which is comprised of Occludin and claudins.

It is to be understood herein, that if a "range" or "group of substances" is mentioned with respect to a particular characteristic (e.g. amino acid groups, temperature, pressure, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to polypeptides, a polypeptide analogue comprising a particular sequence and having an addition of at least one amino acid to its amino-terminus or to its carboxy terminus is to be understood as specifically incorporating each and every individual possibility, such as for example one, two, three, ten, eighteen, forty, etc. Similarly, a polypeptide analogue having at least 90% of its amino acid sequence identical to a particular amino acid sequence is to be understood as specifically incorporating each and every individual possibility (excluding 100%), such as for example, a polypeptide analogue having 90%, 90.5%, 91%, 93.7%, 97%, 99%, etc., of its amino acid sequence identical to a particular amino acid sequence.

Polypeptide Constructs

The present disclosure relates to recombinant fusion proteins that target claudin proteins in tight junctions and uses thereof to transiently disrupt tight junctions for therapeutic applications. The present inventors have found that fusion proteins comprising C-CPE and the EL2 loop of a claudin can specifically target the same claudin at a tight junction. This targeting acts to remove the claudin protein, thereby disrupting the tight junction. Importantly, the disruption is reversible, since after removal of the fusion protein, the claudin protein is restored by the cells, restoring the integrity of the tight junction.

In particular, we demonstrate herein the development of a polypeptide construct, termed "His::NT::C-CPE::Cldn11EL2" that, when injected into mouse testes, 1) reduces the expression of Cldn11 in the BTB tight junctions; 2) disrupts the BTB; and 3) improves SSC engraftment in the testes. These findings suggest that targeting Cldn11 could provide a treatment to restore male fertility after toxic therapies by disrupting the BTB and thereby improving SSC engraftment in the testes. Similarly, other claudin proteins at other tight junctions can be targeted to allow transient disruption of paracellular barriers. Polypeptide constructs provided herein can therefore have wide clinical application.

Claudins are a family of proteins with close to 30 members that comprise tight junctions. Claudins are structurally characterized by two extracellular loops (EL1 and EL2) and two intracellular termini [14,16]. A schematic drawing of a claudin protein is shown in FIG. 1(C). EL1 determines the size and charge selectivity of the barrier and EL2 interacts with claudin molecules on adjacent cells [9,17]. Claudins have tissue-specific and spatially-restricted expression. The barrier properties of tight junctions are determined by the claudins expressed therein. The claudin protein to be used and targeted in polypeptides of the present technology is not particular limited; it should be understood that any claudin may be targeted including, for example and without limitation: claudin 1, 2, 3, 4, 5, 6, 7, 8, 9, 10, 11, 12, 14, 15, 16 or 19, or a combination thereof. Selection of the claudin to be targeted will depend on the tissue/tight junction being targeted. Representative claudins and their expression profiles are shown in Table 1.

TABLE 1

Representative claudin proteins.

| Claudin Target | Human Expression |
|---|---|
| Cldn1 | Skin, liver |
| Cldn2 | Kidney, intestine |
| Cldn3 | Intestine, BTB, BBB and neural tube |
| Cldn4 | Intestine, neural tube |
| Cldn5 | BBB, endothelium |
| Cldn6 | Brain, ovary |
| Cldn7 | Lungs, pancreas, intestine, liver |
| Cldn8 | BTB, neural tube |
| Cldn9 | Brain, liver, ovary, pancreas |
| Cldn10 | Kidney, oligodendrocytes |
| Cldn11 | BTB, oligodendrocytes, bone |
| Cldn12 | Intestine, liver, kidney, brain |
| Cldn14 | Kidney, ear, liver |
| Cldn15 | Intestine |
| Cldn16 | Kidney |
| Cldn19 | Kidney, brain, eye, ovary |

Sequences of the EL2 loops of representative claudins are given in Table 2.

Polypeptides of the present technology may comprise the entire claudin EL2 loop, or a portion or fragment thereof that retains the desired claudin binding and/or targeting properties. In some embodiments, the EL2 loop comprises or consists of the entire EL2 loop, or a functionally equivalent variant, analogue, derivative or fragment thereof. In some embodiments, the EL2 loop comprises or consists of a portion of the EL2 loop sufficient for specific binding and/or targeting of the desired claudin. For example, the EL2 loop may comprise or consist of a 13 amino acid-long portion that specifically binds the desired claudin. In some embodiments, the EL2 loop comprises or consists of the sequence set forth in any one of SEQ ID NOs: 7-12 and 15-40, or a functionally equivalent sequence having at least 80%, at least 90%, at least 95%, at least 98%, or at least 99% identity thereto.

In some embodiments, the EL2 sequence is the human sequence, for targeting a human claudin protein in a human subject. In other embodiments, the EL2 sequence may be the sequence from another mammal, e.g., mouse, depending on the subject.

*Clostridium perfringens* enterotoxin (CPE) is a single polypeptide that causes symptoms associated with food poisoning. CPE has a claudin binding domain located at the C-terminus (C-CPE) and has been reported to interact with Cldn3, 4, 6, 7, 8, and 14 but not with Cldn1, 2, 5, or 10 [20]. The evidence thus far reported indicates that C-CPE also does not bind to Cldn11 [21]. A schematic drawing of a CPE protein is shown in FIG. 1(D). The C-CPE domains have been identified by crystallography and mutational analyses [17,20,29]. In polypeptide constructs of the present technology, the N-terminal domain that possesses cytotoxic activity is removed, leaving the C-terminal domain (C-CPE; amino acids 185-319). The C-terminal domain also includes a claudin-binding domain (amino acids 290-319). To provide specific targeting of a desired claudin, the claudin-binding domain is removed, and replaced with the claudin EL2 loop. The C-CPE region in polypeptide constructs of the present technology therefore comprises amino acids 185-290 of the *Clostridium perfringens* enterotoxin, or a functionally equivalent variant, analogue, derivative or fragment thereof, or a functionally equivalent sequence having at least 80%, at least 90%, at least 95%, at least 98%, or at least 99% identity thereto. In some embodiments, the C-CPE region in polypeptide constructs of the present technology comprises or consists of the sequence set forth in SEQ ID NO: 14, or a functionally equivalent sequence having at least 80%, at least 90%, at least 95%, at least 98%, or at least 99% identity thereto.

Sequences of the C-CPE regions of representative claudins are given in Table 2.

In accordance with the present technology, polypeptide constructs may also comprise one or more additional region. For example, polypeptide constructs may comprise one or more of a detectable tag, such as a His tag or a fluorescent tag (GFP) and the like; a tag for purification, such as a His tag or a GST tag; a tag for increasing solubility of the polypeptide such as the N-terminal domain from Euprosthenops australis major ampullate spidroin 1 (NT); a TEV protease recognition sequence; and the like. Additional regions to be included in polypeptide constructs are not particularly limited; many tags used for detection, purification, solubilization, stabilization, etc. are known, and may be used in accordance with art-recognized techniques to facilitate expression, purification, manufacturing, stabilization, solubilization, detection, etc. of the polypeptide construct.

In some embodiments, the polypeptide construct comprises a tag to facilitate purification, such as, for example and without limitation, a MBP, GST, HIS, Halo, Strep, Flag, HA, or myc tag. Other tags are known; see, for example, Costa et al., 2014, Frontiers in Microbiology, doi: 10.3389/fmicb.2014.00063, the entire contents of which are hereby incorporated by reference in their entirety.

In some embodiments, the polypeptide construct comprises a tag to improve solubility, such as, for example and without limitation, a SUMO, TRX, or NT tag. NT tags are described in Kronqvist et al., 2017, Nature communications, DOI: 10.1038/ncomms15504, the entire contents of which are hereby incorporated by reference in their entirety.

In some embodiments, the polypeptide construct comprises a TEV protease recognition sequence.

Representative sequences in accordance with certain embodiments of the present technology are given in Table 2. Sequences are shown, from left to right, in the N-terminal to C-terminal direction.

TABLE 2

Exemplary sequences.

| SEQ ID NO. | Description | Sequence |
|---|---|---|
| 1 | Mouse His::NT::C-CPE::Cldn1EL2 | MGHHHHHHMSHTTPWTNPGLAENFMNSFMQGLSSMPG FTASQLDKMSTIAQSMVQSIQSLAAQGRTSPNDLQAL NMAFASSMAEIAASEEGGGSLSTKTSSIASAMSNAFL QTTGVVNQPFINEITQLVSMFAQAGMNDVSAGTGENL YFQGRCVLTVPSTDIEKEILDLAAATERLNLTDALNS NPAGNLYDWRSSNSYPWTQKLNLHLTITATGQKYRIL ASKIVDFNIYSNNFNNLVKLEQSLGDGVKDHYVDIST AWYGNRIVQEFYDPLTPINARYEFGQ |
| 2 | Mouse His::NT::C-CPE::Cldn2EL2 | MGHHHHHHMSHTTPWTNPGLAENFMNSFMQGLSSMPG FTASQLDKMSTIAQSMVQSIQSLAAQGRTSPNDLQAL NMAFASSMAEIAASEEGGGSLSTKTSSIASAMSNAFL QTTGVVNQPFINEITQLVSMFAQAGMNDVSAGTGENL YFQGRCVLTVPSTDIEKEILDLAAATERLNLTDALNS NPAGNLYDWRSSNSYPWTQKLNLHLTITATGQKYRIL ASKIVDFNIYSNNFNNLVKLEQSLGDGVKDHYVDISS SWNLHGILRDFYSPLVPDSMKFEIGE |
| 3 | Mouse His::NT::C-CPE::Cldn3EL2 | MGHHHHHHMSHTTPWTNPGLAENFMNSFMQGLSSMPG FTASQLDKMSTIAQSMVQSIQSLAAQGRTSPNDLQAL NMAFASSMAEIAASEEGGGSLSTKTSSIASAMSNAFL QTTGVVNQPFINEITQLVSMFAQAGMNDVSAGTGENL YFQGRCVLTVPSTDIEKEILDLAAATERLNLTDALNS NPAGNLYDWRSSNSYPWTQKLNLHLTITATGQKYRIL ASKIVDFNIYSNNFNNLVKLEQSLGDGVKDHYVDISS SIIRDFYNPLVPEAQKREMGA |
| 4 | Mouse His::NT::C-CPE::Cldn5EL2 | MGHHHHHHMSHTTPWTNPGLAENFMNSFMQGLSSMPG FTASQLDKMSTIAQSMVQSIQSLAAQGRTSPNDLQAL NMAFASSMAEIAASEEGGGSLSTKTSSIASAMSNAFL QTTGVVNQPFINEITQLVSMFAQAGMNDVSAGTGENL YFQGRCVLTVPSTDIEKEILDLAAATERLNLTDALNS NPAGNLYDWRSSNSYPWTQKLNLHLTITATGQKYRIL ASKIVDFNIYSNNFNNLVKLEQSLGDGVKDHYVDISR EFYDPTVPVSQKYEL |

TABLE 2-continued

Exemplary sequences.

| SEQ ID NO. | Description | Sequence |
|---|---|---|
| 5 | Mouse His::NT::C-CPE::Cldn8EL2 | MGHHHHHHMSHTTPWTNPGLAENFMNSFMQGLSSMPG FTASQLDKMSTIAQSMVQSIQSLAAQGRTSPNDLQAL NMAFASSMAEIAASEEGGGSLSTKTSSIASAMSNAFL QTTGVVNQPFINEITQLVSMFAQAGMNDVSAGTGENL YFQGRCVLTVPSTDIEKEILDLAAATERLNLTDALNS NPAGNLYDWRSSNSYPWTQKLNLHLTITATGQKYRIL ASKIVDFNIYSNNFNNLVKLEQSLGDGVKDHYVDISS IIRDFYNPLVDVALKRELGEALY |
| 6 | Mouse His::NT::C-CPE::Cldn11EL2 | MGHHHHHHMSHTTPWTNPGLAENFMNSFMQGLSSMPG FTASQLDKMSTIAQSMVQSIQSLAAQGRTSPNDLQAL NMAFASSMAEIAASEEGGGSLSTKTSSIASAMSNAFL QTTGVVNQPFINEITQLVSMFAQAGMNDVSAGTGENL YFQGRCVLTVPSTDIEKEILDLAAATERLNLTDALNS NPAGNLYDWRSSNSYPWTQKLNLHLTITATGQKYRIL ASKIVDFNIYSNNFNNLVKLEQSLGDGVKDHYVDISS SHREITIVSFGYSLY |
| 7 | Human Cldn1 EL2 | TAWYGNRIVQEFYDPMTPVNARYEFGQ |
| 8 | Human Cldn2 EL2 | WNLHGILRDFYSPLVPDSMKFEIGE |
| 9 | Human Cldn3EL2 | WSANTIIRDFYNPVVPEAQKREM |
| 10 | Human Cldn5EL2 | VREFYDPSVPVSQKYE |
| 11 | Human Cldn8EL2 | WVANAIIRDFYNSIVNVAQKRELGEALY |
| 12 | Human Cldn11EL2 | CAHRETTIVSFGYS |
| 13 | NT region | SHTTPWTNPGLAENFMNSFMQGLSSMPGFTASQLDKM STIAQSMVQSIQSLAAQGRTSPNDLQALNMAFASSMA EIAASEEGGGSLSTKTSSIASAMSNAFLQTTGVVNQP FINEITQLVSMFAQAGMNDV |
| 14 | C-CPE region | RCVLTVPSTDIEKEILDLAAATERLNLTDALNSNPAG NLYDWRSSNSYPWTQKLNLHLTITATGQKYRILASKI VDFNIYSNNFNNLVKLEQSLGDGVKDHYVDIS |
| 15 | Mouse Cldn1 EL2 | TAWYGNRIVQEFYDPLTPINARYEFGQ |
| 16 | Mouse Cldn2 EL2 | WNLHGILRDFYSPLVPDSMKFEIGE |
| 17 | Mouse Cldn3 EL2 | WSANTIIRDFYNPLVPEAQKREM |
| 18 | Mouse Cldn5 EL2 | REFYDPTVPVSQKYEL |
| 19 | Mouse Cldn8 EL2 | WVANSIIRDFYNPLVDVALKRELGEALY |
| 20 | Mouse Cldn11 EL2 | CAHREITIVSFGYS |
| 21 | Mouse Cldn4 EL2 | WTAHNVIRDFYNPMVASGQKREM |
| 22 | Mouse Cldn6 EL2 | WTAHSIIQDFYNPLVADAQKRELGAS |
| 23 | Mouse Cldn7 EL2 | GHQIVTDFYNPLTPMNVKYE |
| 24 | Mouse Cldn9 EL2 | WTAHAIIQDFYNPLVAEALKRE |

TABLE 2-continued

Exemplary sequences.

| SEQ ID NO. | Description | Sequence |
|---|---|---|
| 25 | Mouse Cldn10 EL2 | LYANKITTEFFDPLYMEQKYELGA |
| 26 | Mouse Cldn12 EL2 | YNSHLNRKFEPVFTFDYA |
| 27 | Mouse Cldn14 EL2 | SWTTNDVVQNFYNPLLPSGMKFEIGQ |
| 28 | Mouse Cldn15 EL2 | NITTDFFNPLYAGTKYELG |
| 29 | Mouse Cldn16 EL2 | WYAVDVYVERSSLVLHNIFLGIQYKFGWSCWLG |
| 30 | Mouse Cldn19 EL2 | WYATLVTQEFFNPSTPVNARYE |
| 31 | Human Cldn4 EL2 | TAHNIIQDFYNPLVASGQKREM |
| 32 | Human Cldn6 EL2 | WTAHAIIRDFYNPLVAEAQKREL |
| 33 | Human Cldn7 EL2 | WYGHQIVTDFYNPLIPTNIKYE |
| 34 | Human Cldn9 EL2 | WTAHAIIQDFYNPLVAEALKRE |
| 35 | Human Cldn10 EL2 | LYANKITTEFFDPLFVEQKYELGA |
| 36 | Human Cldn12 EL2 | YNIHLNKKFEPVFSFDYA |
| 37 | Human Cldn14 EL2 | SWTTNDVVQNFYNPLLPSGMKFEIGQ |
| 38 | Human Cldn15 EL2 | NITRDFFDPLYPGTKYELG |
| 39 | Human Cldn16 EL2 | WYAVDVYVERSTLVLHNIFLGIQYKFGWSCWLG |
| 40 | Human Cldn19 EL2 | WYATLVTQEFFNPSTPVNARYE |
| 41 | His::NT::TEV region | MGHHHHHHMSHTTPWTNPGLAENFMNSFMQGLSSMPG FTASQLDKMSTIAQSMVQSIQSLAAQGRTSPNDLQAL NMAFASSMAEIAASEEGGGSLSTKTSSIASAMSNAFL QTTGVVNQPFINEITQLVSMFAQAGMNDVSAGTGENL YFQG |

As may be appreciated, a number of modifications may be made to the polypeptides of the present technology without deleteriously affecting the biological activity (e.g., claudin binding and/or targeting) of the polypeptides. Polypeptides of the present technology comprise for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications comprise for example, without limitation, acetylation, acylation, addition of acetomidomethyl (Acm) group, ADP-ribosylation, amidation, covalent attachment to flavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Other types of polypeptide modification may comprise for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide. Polypeptides of the present technology comprise for example, biologically active mutants, variants, fragments, chimeras, and analogues; fragments encompassing amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may have the biological properties of polypeptides of the present invention which comprise for example (without being restricted to the present examples) to facilitate claudin binding and/or targeting, to increase stability of the polypeptide, to improve manufacturing (yield, purification), and the like.

Examples of substitutions may include those which are conservative (i.e., wherein a residue is replaced by another of the same general type). As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same group as that of the amino acid being replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA may also be made. For example, alternative residues include the omega amino acids of the formula $NH_2(CH_2)_nCOOH$ wherein n is 2-6. These are neutral nonpolar amino acids, as are sarcosine, t-butyl alanine, t-butyl glycine, N-methyl isoleucine, and norleucine. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that mutants or variants may be generated by substitutional mutagenesis and retain the biological activity of the polypeptides of the present invention. These variants may for example have at least one amino acid residue in the protein molecule removed and a different residue inserted in its place (one or more nucleotide in the DNA sequence is changed for a different one using known molecular biology techniques, giving a different amino acid upon translation of the corresponding messenger RNA to a polypeptide).

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Amino acid sequence insertions (e.g., additions) include amino and/or carboxyl-terminal fusions ranging in length from one residues to polypeptides containing a hundred or more residues, as well as intrasequence insertions of single or multiple amino acid residues. Other insertional variants include the fusion of the N- or C-terminus of the protein to a homologous or heterologous polypeptide forming a chimera. Chimeric polypeptides (i.e., chimeras, polypeptide analogues) comprise a sequence of the polypeptides of the present invention fused to homologous or heterologous sequence. Said homologous or heterologous sequence encompass those which, when formed into a chimera with the polypeptides of the present invention retain one or more biological or immunological properties.

Other types of polypeptide modification include amino acids sequence deletions (e.g., truncations). Those generally range from about 1 to 30 residues, more preferably about 1 to 10 residues and typically about 1 to 5 residues.

Functionally equivalent mutants, variants, analogues, derivatives and fragments of polypeptide constructs of the present technology are also encompassed.

Mutant polypeptides generally possess one or more mutations, which are deletions (e.g., truncations), insertions (e.g., additions), or substitutions of amino acid residues. Mutants can be either naturally occurring (that is to say, purified or isolated from a natural source) or synthetic (for example, by performing site-directed mutagenesis on the encoding DNA or made by other synthetic methods such as chemical synthesis).

The term "variant", as used herein, is a polynucleotide or polypeptide that differs from the reference polynucleotide or polypeptide respectively, but is functionally equivalent. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion and truncations in the polypeptide encoded by the reference sequence, as discussed herein. A typical variant of a polypeptide differs in amino acid sequence from another, reference polypeptide. Generally, differences are limited so that the sequence of the reference polypeptide and the variant are closely similar overall and, in many regions, identical. A variant and reference polypeptide may differ in amino acid by one or more substitutions, additions, deletions, or any combination therefore. A substituted or inserted amino acid residue may or may not be one encoded by the genetic code. A variant polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

Amino acid sequence variants may be prepared by introducing appropriate nucleotide changes into DNA, or by in vitro synthesis of the desired polypeptide. Such variants include, for example, deletions, insertions, or substitutions of residues within the amino acid sequence. A combination of deletion, insertion and substitution can be made to arrive at the final construct, provided that the final protein product possesses the desired biological activity, or characteristics. The amino acid changes also may alter posttranslational processes such as changing the number or position of the glycosylation sites, altering the membrane anchoring characteristics, altering the intra-cellular location by inserting, deleting or otherwise affecting the transmembrane sequence of the native protein, or modifying its susceptibility to proteolytic cleavage.

Unless otherwise indicated, the recombinant DNA techniques utilized in the present invention are standard procedures, known to those skilled in the art. Example of such techniques are explained in the literature in sources such as J. Perbal, A Practical Guide to Molecular Cloning, John Wiley and Sons (1984), J. Sambrook et al., Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present) and are incorporated herein by reference.

The polypeptide constructs of the present technology include biologically active fragments and analogues thereof; fragments encompass amino acid sequences having truncations of one or more amino acids, wherein the truncation may originate from the amino terminus, carboxy terminus, or from the interior of the protein. Analogues of the invention involve an insertion or a substitution of one or more amino acids.

A host cell transformed or transfected with nucleic acids encoding a polypeptide construct of the present technology are also encompassed. Any host cell which produces a polypeptide may be used. Specific examples include bacterial, yeast, plant, insect or mammalian cells. In addition, a polypeptide construct may be produced in transgenic animals. Transformed or transfected host cells and transgenic animals are obtained using materials and methods that are routinely available to one skilled in the art. Host cells may contain nucleic acid sequences encoding a polypeptide construct. In addition, nucleic acid fragments, variants and analogues which encode a polypeptide construct or functional equivalent in accordance with the present technology may also be resident in host expression systems.

Polypeptide constructs can be made according to methods present in the art. The proteins of the present technology may be prepared from bacterial cell extracts, or through the use of recombinant techniques. In general, a polypeptide construct according to the invention can be produced by transformation (transfection, transduction, or infection) of a host cell with all or part of a polypeptide-encoding DNA fragment in a suitable expression vehicle. Suitable expression vehicles include: plasmids, viral particles, and phages. For insect cells, baculovirus expression vectors are suitable. The entire expression vehicle, or a part thereof, can be integrated into the host cell genome. In some circumstances, it is desirable to employ an inducible expression vector.

Those skilled in the field of molecular biology will understand that any of a wide variety of expression systems can be used to provide the recombinant protein. The precise host cell used is not critical to the present technology. The polypeptide construct may be produced in a prokaryotic host (e.g., *E. coli* or *B. subtilis*) or in a eukaryotic host (e.g., *Saccharomyces* or *Pichia*; mammalian cells, e.g., COS, NIH 3T3, CHO, BHK, 293, or HeLa cells; or insect cells). Proteins and polypeptides may also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.). The methods of transformation or transfection and the choice of expression vehicle will depend on the host system selected.

The host cells harboring the expression vehicle can be cultured in conventional nutrient media adapted as need for activation of a chosen gene, repression of a chosen gene, selection of transformants, or amplification of a chosen gene. One expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. Many mammalian expression systems are known.

In mammalian host cells, a number of viral-based expression systems can also be utilized. In cases where an adenovirus is used as an expression vector, the nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a polypeptide construct in infected hosts.

Specific initiation signals may also be required for efficient translation of inserted nucleic acid sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and the like. Alternatively, a polypeptide construct can be produced by a stably-transfected mammalian cell line.

Compositions and Methods of Use

In another broad aspect, there are provided pharmaceutical compositions comprising a polypeptide construct described herein, or a pharmaceutically acceptable salt thereof, and a pharmaceutically acceptable carrier, diluent or excipient.

The preparation of pharmaceutical compositions can be carried out as known in the art (see, for example, Remington: The Science and Practice of Pharmacy, 20$^{th}$ Edition, 2000). For example, a therapeutic polypeptide and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of a subject, e.g., humans and animals, without undue toxicity, irritation, allergic response, and the like, and are commensurate with a reasonable benefit/risk ratio.

A pharmaceutically acceptable carrier may include any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier may be suitable for intravenous, intraperitoneal, intramuscular, sublingual or oral administration. In other embodiments, the carrier is suitable for topical administration or for administration via inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated. Supplementary active compounds can also be incorporated into the compositions. For example, a pharmaceutical composition provided herein may further comprise at least one additional therapeutic agent.

A pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating a polypeptide construct provided herein, in the required amount in an appropriate solvent with one or a combination of ingredients enumerated above, as required, followed by filtered sterilization. Generally, dispersions are prepared by incorporating the active agent into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Agents may also be formulated with one or more additional compounds that enhance their solubility.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound for the intended use. Dosages are discussed further below.

The term "subject" as used herein includes humans, non-human primates, agricultural animals, experimental animals, and companion animals, including without limitation monkeys, cows, rabbits, sheep, goats, pigs, horses, dogs, cats, rats, mice, and transgenic species thereof. In particular embodiments, the subject is a mammal. In one embodiment, the subject is a human.

In some embodiments, a subject is in need of treatment by the methods provided herein, and is selected for treatment based on this need. A subject in need of treatment is art-recognized, and includes subjects that have been identified as having a disease or condition (e.g., infertility), or having a symptom of such a disease or condition, or being at risk of such a disease or condition, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder). In some embodiments, a subject may be an individual who has previously undergone a toxic therapeutic treatment, such as an anti-cancer treatment, e.g., chemotherapy or radiotherapy. In some embodiments, a subject may be an individual in need of delivery of a therapeutic agent or drug across a paracellular barrier such as the BBB, BTB, intestinal barrier, or the kidney nephronic barrier. In some embodiments, a subject may be an individual suffering from a neurological, an intestinal or a renal disease or condition.

As used herein, "treating" or "treatment" of a disease or condition refers, in some embodiments, to ameliorating at least one disease or condition (i.e., arresting or reducing the development of a disease or condition or at least one of the clinical symptoms thereof). In certain embodiments "treating" or "treatment" refers to ameliorating at least one physical parameter, such as tumor size, growth, or migration. In certain embodiments, "treating" or "treatment" refers to inhibiting or improving a disease or condition, either physically (e.g., stabilization of a discernible symptom), physiologically (e.g., stabilization of a physical parameter), or both. In certain embodiments, "treating" or "treatment" refers to delaying the onset (or recurrence) of a disease or condition. The term "treating" or "treatment" may refer to any indicia of success in the treatment or amelioration of a disease or condition, including any objective or subjective parameter such as abatement; remission; diminishing of symptoms or making the disease or condition more tolerable to the subject; improving a subject's physical or mental well-being, such as reducing pain experienced by the patient; and, in some situations additionally improving at least one parameter of a disease or condition As used herein, "preventing" or "prevention" is intended to refer at least to the reduction of the likelihood of, or the risk of, or susceptibility to acquiring a disease or disorder (i.e., causing at least one of the clinical symptoms of the disease not to develop in a patient that may be exposed to or predisposed to or at risk of the disease but does not yet experience or display symptoms of the disease). The term "prevention" or "preventing" is also used to describe the administration of a compound or composition described herein to a subject who is at risk of (or susceptible to) such a disease or condition. Subjects amenable to treatment for prevention of a disease or condition include individuals at risk of the disease or condition but not showing symptoms, as well as patients presently showing symptoms.

In some embodiments, treatment or prevention are within the context of the present invention if there is a measurable difference between the performances of subjects treated using the polypeptide constructs, compositions and methods provided herein as compared to members of a placebo group, historical control, or between subsequent tests given to the same subject.

The term "effective amount" as used herein means that amount or dose of a polypeptide construct or composition, upon single or multiple dose administration to a subject, which provides the desired effect (e.g., the desired biological or medicinal response) in the subject being treated. In some embodiments, an effective amount is an amount or dose of a polypeptide construct or composition that transiently disrupts a tight junction in a tissue in a subject, as described herein. In some embodiments, an effective amount is an amount or dose of a compound or composition that enhances delivery of a therapeutic agent, enhances stem cell transplantation or engraftment, or treats infertility, as described herein.

It should be understood that the dosage or amount of a polypeptide construct and/or composition used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). For example, dosing and administration regimens depend on the nature and the severity of the disorder to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Thus the dose(s) of a polypeptide construct or composition will vary depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined as known in the art. When one or more of the polypeptide constructs of the invention is to be administered to humans, a physician may for example, prescribe a relatively low dose at first, subsequently increasing the dose until an appropriate response is obtained.

There are no particular limitations on the dose of each of the compounds for use in compositions provided herein. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg or about 250 mg, and, for example, daily or twice daily, or lower or higher amounts.

In some embodiments, the dose range for adult humans is generally from 0.005 mg to 10 g/day orally. Tablets or other forms of presentation provided in discrete units may conveniently contain an amount of a compound (e.g., of Formula I or Formula II) which is effective at such dosage or as a multiple of the same, for instance, units containing 5 mg to 500 mg, usually around 10 mg to 200 mg. A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg) of a compound described herein.

Administration of polypeptide constructs and compositions provided herein can be carried out using known procedures, at dosages and for periods of time effective to achieve a desired purpose. Dosage regimens can be adjusted to provide the optimum therapeutic response. For example, several divided doses may be administered daily or the dose may be proportionally reduced as indicated by the exigencies of the therapeutic situation. Further, a compound or composition may be administered using any suitable route or means, such as without limitation via oral, parenteral, intravenous, intraperitoneal, intramuscular, sublingual, topical, or nasal administration, via inhalation, or via such other routes as are known in the art.

Without wishing to be limited by theory, the present inventors contemplate that polypeptide constructs and compositions provided herein may be used for a wide range of therapeutic applications, including without limitation: facilitating delivery of a therapeutic agent across a paracellular barrier such as the blood-brain-barrier, the BTB, the intestinal barrier, the kidney nephronic barrier, and the like; increasing efficacy of cellular transplantation including stem cells; increasing cell engraftment after transplantation; drug delivery to a tissue; drug delivery to a solid tumor mass; and other applications in which transient disruption of a tight junction in a tissue is useful.

In some embodiments, there are provided methods of improving spermatogonial stem cell (SSC) transplantation efficiency and/or restoring male fertility comprising administration of a claudin-11 targeting polypeptide construct to a subject in need thereof. In an embodiment, the claudin-11 targeting polypeptide construct comprises or consists of the His::NT::C-CPE::Cldn11EL2 polypeptide construct or a functionally equivalent variant, analogue, derivative or fragment thereof. In some embodiments, the claudin-11 targeting polypeptide construct has the sequence set forth in SEQ ID NO: 6, or a functionally equivalent sequence at least 80%, at least 90%, at least 95%, at least 98%, or at least 99% identical thereto.

Kits

Polypeptide constructs and compositions provided herein, as well as nucleic acids and vectors for expressing the polypeptide constructs, may be packaged as part of a kit, optionally including a container (e.g. packaging, a box, a vial, etc). The kit may be commercially used according to the methods described herein and may include instructions for use in such methods. Additional kit components may include acids, bases, buffering agents, inorganic salts, solvents, antioxidants, preservatives, or metal chelators. The additional kit components may be present as pure compositions, or as aqueous or organic solutions that incorporate one or more additional kit components. Any or all of the kit components optionally further comprise buffers.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. Development of a Cldn11-Targeting Protein

The discovery that SSC transplantation leads to the recovery of fertility in sterile mice [22-24] suggested that this technique could be used to restore fertility in cancer survivors [25]. Our methods are based on harvesting SSCs for cryopreservation before cancer therapy, followed by transplantation into the testes after therapy. To improve SSC transplantation efficiency, we hypothesized that targeting Cldn11 might disrupt the BTB, thereby improving fertility following SSC transplantation. Substances that disrupt the BTB and inhibit Cldns have been identified; however, none of them are specific to Cldn11. A recent report demonstrated that acyline, a gonadotrophin releasing hormone analogue, reversibly disrupts the BTB, resulting in reduced Cldn5 expression, increased SSC colonization in infertile recipients, and sired offspring [19]. Moreover, *Clostridium perfringens* enterotoxin (CPE), which is a single polypeptide that causes symptoms associated with food poisoning, has a claudin binding domain located at the C-terminus (C-CPE) and has been reported to interact with Cldn3, 4, 6, 7, 8, and 14 but not with Cldn1, 2, 5, or 10 [20]. The evidence thus far reported indicates that C-CPE also does not bind to Cldn11 [21]. Collectively, these findings supported targeting Cldn11 as a potential strategy for the restoration of male fertility.

We sought to design a protein capable of increasing SSC transplantation efficiency that could act by reducing expression of Cldn11 at the BTB tight junctions, thereby disrupting the BTB and improving SSC transplantation efficiency, in order to restore fertility. Such a protein could be used, for example, in a method for restoring fertility in which SSCs are harvested for cryopreservation before anti-cancer therapy, and the SSCs are then transplanted into the testes with the protein, after therapy. A schematic diagram illustrating such a method is shown in FIG. 1.

Figure 4:
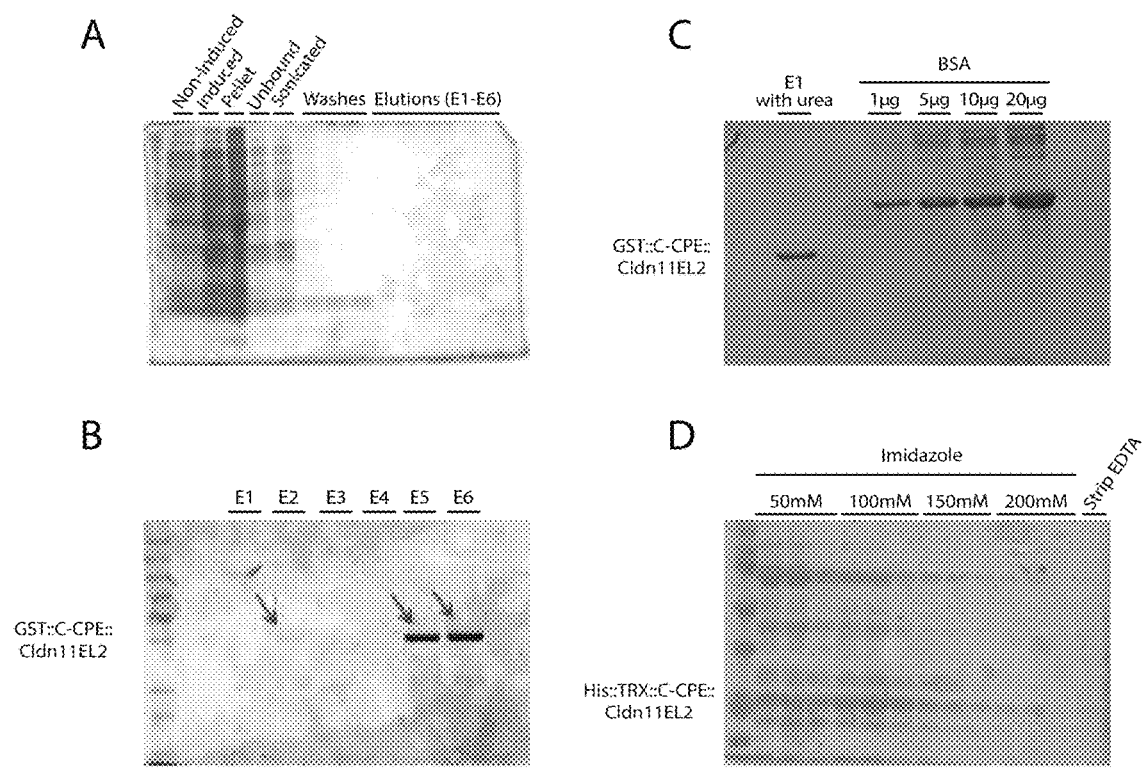
FIG. 4 shows protein purification results, using electrophoresis, of preliminary Cldn11-targeting proteins produced which were either insoluble or yielded protein quantities too small to allow us to proceed with further biological assessment in vivo. (A) Purification of GST::C-CPE::Cldn11EL2 using STE buffer; no soluble protein was eluted. (B) Purification of GST::C-CPE::Cldn11EL2 using Sarkosyl buffer; soluble protein was eluted. (C) Protein purification of GST::C-CPE::Cldn11EL2 in 2 L of culture using 8M of urea to denature the protein, relative to known concentrations of bovine serum albumin (BSA); only 1 ug/mL and 1.6 mg of total protein was obtained. (D) Protein purification of His::TRX::C-CPE::Cldn11EL2; elutions with increased concentrations of imidazole caused the TRX protein to elute with very low concentrations (<100 uM), such that it was lost during washes.

Using the knowledge that the C-terminus of *Clostridium perfringens* enterotoxin (C-CPE) is capable of 1) interacting with and internalizing claudins, 2) inducing claudin removal from tight junctions, and 3) disrupting tight junctions [21, 26], we investigated whether C-CPE could transiently disrupt tight junctions in the BTB, thereby improving SSC transplantation efficiency. Importantly, C-CPE is not cytotoxic [26,27], and upon withdrawal of C-CPE treatment, claudins repopulate tight junctions and restore its normal barrier properties [27]. To this end, we have produced bacterially-expressed C-CPE as a chimeric protein with GST (glutathione S-transferase) and confirmed that our home-made C-CPE disrupts tight junctions in chick embryos [28]. This suggests that C-CPE removes C-CPE sensitive claudins, which is sufficient to increase SSC engraftment. However, since C-CPE does not target Cldn11, which is critical for the formation of BTB tight junctions [18], we predicted that the generation of a reagent that reduces the expression of Cldn11 at the BTB tight junction (i.e., reversibly removes Cldn11 from the BTB tight junction) would yield marked improvements of SSC transplantation efficiency.

To develop this Cldn11-targeting protein, we began by swapping the claudin-binding domain of C-CPE with the EL2 binding domain of Cldn11. The C-CPE domains have been identified by crystallography and mutational analyses [17,20,29]. Thus, the first steps in developing our Cldn11-targeting protein included extensive optimization and troubleshooting of the protein purification procedure in order to generate sufficient yields of a soluble protein.

To generate a soluble protein tag, we tested several approaches before optimizing the solubility component of our protein. We initially tested the use of glutathione S transferase (GST) as a purification tag, without adding a solubility tag. The GST::C-CPE::Cldn11EL2 DNA construct was inserted into both pET14bGST and pGEX6PI, which was controlled by a Isopropyl-β-D-thiogalactoside (IPTG) inducible promotor. In order to purify the GST::C-CPE::Cldn11EL2 recombinant protein fragment, the DNA construct was first transformed into *E. coli* BL21 cells and grown to 400 ml culture. This culture was induced using 0.4 mM of IPTG once the culture absorbance reached 0.4, to generate the recombinant protein fragment. The culture was then left overnight at room temperature with constant agitation (250 rpm). Next, protein purification was performed, such that bacterial pellets were lysed in the presence of resuspension buffer (50 mM Tris pH7.5, 150 mM Nacl, 0.1 mM EDTA) and protease inhibitors (1.45 nM Pepsatin A, 2.1 nM Leupeptin, 0.15 nM Aprotinin and 0.57 mM PMSF). After 20-minutes of incubation on ice, detergents were added, and the samples were sonicated (6 times, 30 seconds) and centrifuged at 15,000 rpm for 30 minutes. The resulting supernatant was incubated at 4° C. overnight with Glutathione Sepharose 4B beads in order to pull down the tagged-recombinant protein fragment (hereafter referred to as GST::C-CPE::Cldn11EL2). Washes in washing buffer (50 mM Tris pH7.5 and 0.5M Nacl) were performed 3-4 times on the incubated beads, followed by 10 elutions of a volume equivalent to the beads-bed-volume of elution buffer (50 mM Tris pH7.5, 150 mM Nacl and 10 mM glutathione). In order to evaluate GST::C-CPE::Cldn11EL2 induction and solubility, samples were run on a 10% electrophoresis gel and stained using Coomassie blue. Samples comprised: non-induced, induced (using 0.4 mM IPTG), pellet, unbound, bead washes, and subsequent elutions (FIG. 2). The gels illustrated that although the protein was visibly induced, no soluble protein was eluted; suggesting that this peptide was highly insoluble. Using a longer or shorter C-CPE sequence (186-290aa or 186-303aa) did not change this outcome.

To solubilize GST::C-CPE::Cldn11EL2, we employed alternative protein purification approaches (FIG. 3), where we tested different conditions. "Stars" in FIG. 3 indicate steps that were troubleshooted and required extensive optimization, including: sonication parameters; growth parameters (e.g. temperature and IPTG concentration) and the use of detergents (e.g. SDS (FIG. 4A), Sarkosyl (FIG. 4B), CHAPS or octyl glucoside). Of these, only Sarkosyl increased the quantity of protein eluted in the soluble fraction (FIG. 4B). However, once GST::C-CPE::Cldn11EL2 was dialyzed against PBS to remove the detergent, it precipitated and again became insoluble.

In further attempts to purify a soluble GST::C-CPE::Cldn11EL2, we next tested the use of urea to denature our protein, followed by dialysis to slowly renature the protein. Although this approach generated some soluble GST::C-CPE::Cldn11EL2, the yields were too low (i.e. less than 2 mg of protein was obtained from 2 L of culture media), suggesting that protein insolubility was still hampering our ability to extract larger quantities (FIG. 4C).

We next tested the addition of a TRX solubility tag, which we used with the pSF-OXB20-EKT-TRX vector. To generate the His-tagged recombinant protein fragments, the DNA construct was inserted and transformed using the corresponding vector into *E. Coli* BL21 cells and grown to 400 ml culture. This culture was induced using 0.2 mM of IPTG once the culture absorbance reached 0.3, to generate the recombinant protein fragment. The culture was then left overnight at 22° C. with constant agitation (250 rpm). Next, protein purification was performed, such that bacterial pellets were lysed in the presence of resuspension buffer (50 mM Tris pH7.5, 150 mM NaCl, 10 mM imidazole) and protease inhibitors (1.45 nM Pepsatin A, 2.1 nM Leupeptin, 0.15 nM Aprotinin and 0.57 mM PMSF). After 20 minutes of incubation on ice, sodium deoxycholate and NaCl was added to reach 0.2% and 0.5M respectively. The sample, was then sonicated (9 times, 30 seconds) and centrifuged at 15,000 rpm for 30 minutes. The resulting supernatant was incubated at 4° C. overnight with Ni-NTA agarose beads in order to pull down the tagged-protein. Washes in washing buffer (50 mM Tris pH7.5, 0.5M Nacl and 15 mM imidazole) were performed 3-4 times on the incubated beads, followed by 10 elutions of a volume equivalent to the beads-bed-volume on elution buffer (50 mM Tris pH7.5, 150 mM Nacl and 300 mM imidazole). A Bradford assay was used to determine which elutions carried the purified recombinant protein fragment. Positive elutions were dialyzed overnight against PBS, aliquoted and stored for future use. Although the TRX solubility tag enabled us to extract soluble protein, it was very sensitive to imidazole and it was therefore easily lost during washes (FIG. 4D).

Figure 5:
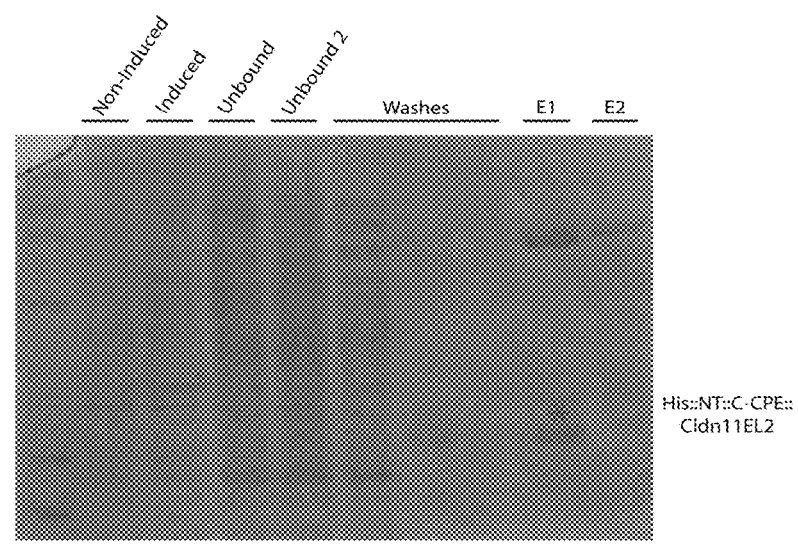
FIG. 5 shows protein purification results for His::NT::C-CPE::Cldn11EL2. Soluble protein was obtained using the NT-tag.
Figure 6:
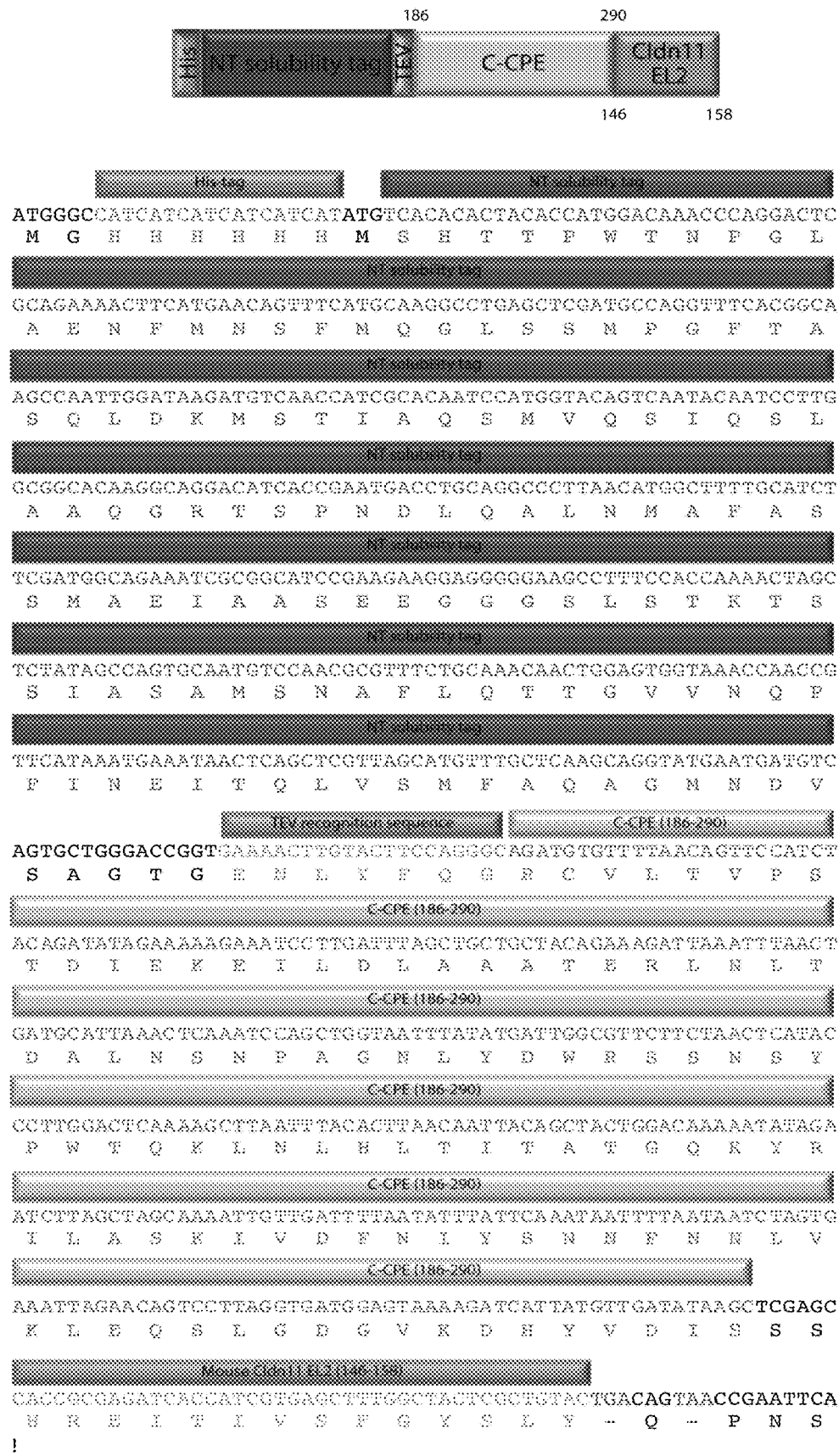
FIG. 6 shows the nucleotide and amino acid sequence of the His::NT::C-CPE::Cldn11EL2 polypeptide, in accordance with certain embodiments, which has been color-coded to differentiate the various domains as follows: His-tag is shown in blue; solubility tag is shown in purple; TEV recognition sequence is shown in orange; C-CPE region is shown in grey; and claudin EL2 domain is shown in green.
Figure 7:
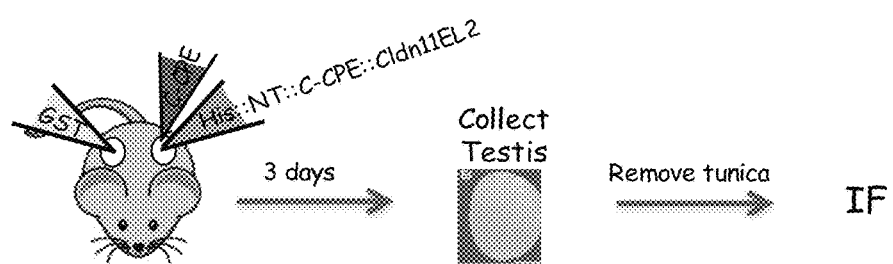
FIG. 7 illustrates that simultaneous co-injection of C-CPE and His::NT::C-CPE::Cldn11EL2 resulted in reduced expression of Cldn8 in the seminiferous tubule tight junctions with no apparent effect on Cldn11. This figure indicates that C-CPE affected Cldn8, and suggests that the transient effect of His::NT::C-CPE::Cldn11EL2 on Cldn11 may have already been complete by day 3. (A) is a schematic illustration of the administration protocol. (B) shows representative immunofluorescent images of the seminiferous tubules stained for Cldn8 (green-left panel) and Cldn11 (green-right panel) and a marker of tight junctions, Zona Occludens 1 (ZO-1) (red).
Figure 7:
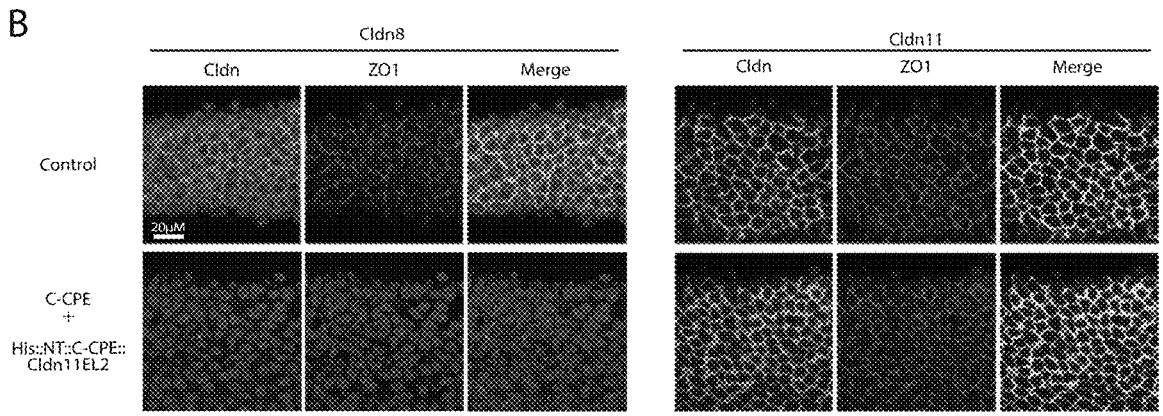
Figure 8:
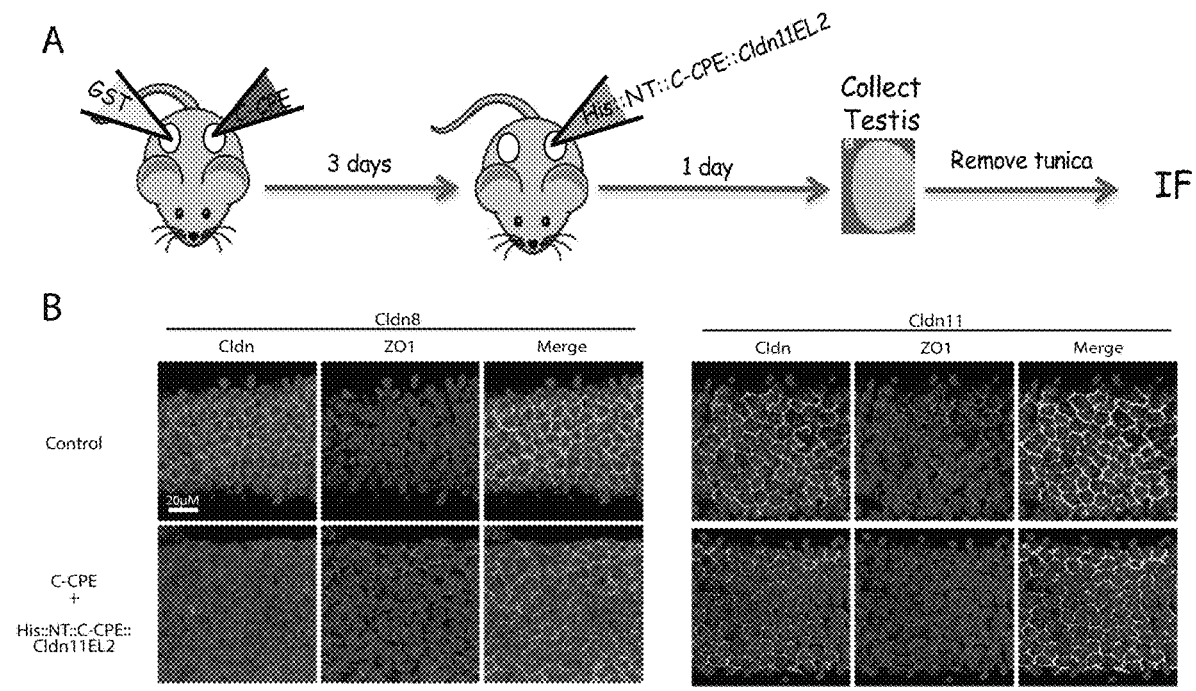
FIG. 8 demonstrates an alternate approach to co-injection. Tandem injection of C-CPE and His::NT:C-CPE:: Cldn11EL2 at day 0 and 3, respectively, resulted in a reduction in the expression of both Cldn8 and Cldn11 in the seminiferous tubule tight junctions on day 4. (A) is a schematic illustration of the administration protocol. (B) shows representative immunofluorescent images of the seminiferous tubules stained for Cldn8 (green-left panel) and Cldn11 (green-right panel) and a marker of tight junctions, zona occludens 1 (ZO-1) (red). These results suggest that the effect of His::NT::C-CPE::Cldn11EL2 on Cldn11 was much more transient than the effect of C-CPE on Cldn8.
Figure 9:
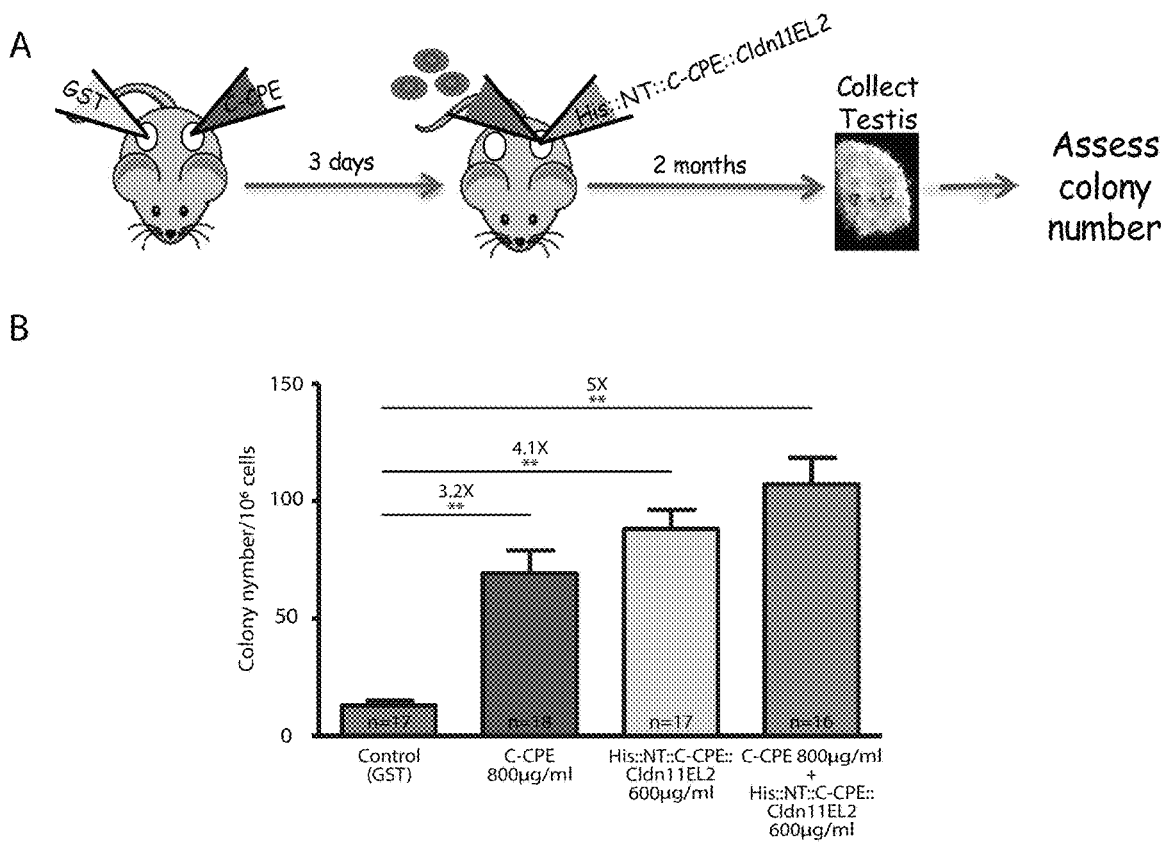
FIG. 9 shows that transplantation of SSCs using His:: NT::C- CPE::Cldn11EL2 alone, or in combination with C-CPE, resulted in a 4.1 and 5-fold increase in SSC transplantation efficiency, respectively. (A) is a schematic illustration of the transplantation protocol using the tandem injection of C-CPE at day 0 and His::NT::C-CPE:: Cldn11EL2 at day3. (B) shows quantification of SSC transplantation efficiency of SSCs under control conditions (GST), or in the presence of equal molar concentrations of C-CPE, His::NT::C-CPE::Cldn11EL2, or a combination of C-CPE and His::NT::C-CPE::Cldn11EL2. Note that His:: NT::C-CPE::Cldn11EL2 alone was at least equivalently effective as C-CPE and gave further benefits in stem cell delivery when used in conjunction with C-CPE.
Figure 10:
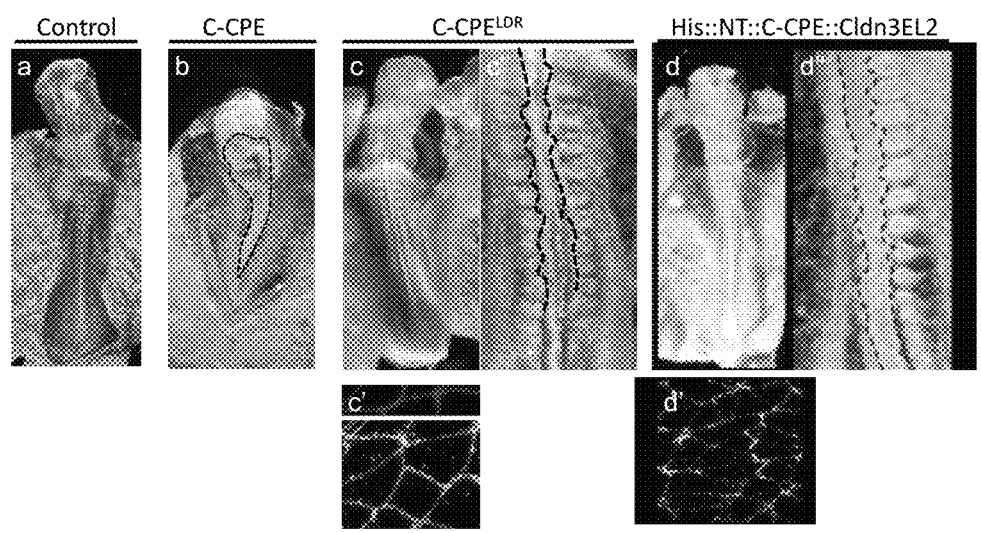
FIG. 10 shows results from experiments with the His:: NT::C-CPE::Cldn3EL2 (NT3) peptide in chick embryos. (a-b) Embryos were cultured in 200 µg/ml GST (a), 200 µg/ml GST-C-CPE (b), 200 µg/ml GST-C-CPE$^{LDR}$ (c), or 200 µg/ml His::NT::C-CPE::Cldn3EL2 (d). Treatment with C-CPE (b) caused severe open neural tube defects along the entire length of the embryo. Treatment with GST-C-CPE$^{LDR}$, a C-CPE variant that specifically targets Cldn3 caused milder open neural tube defects due to failure of the final step in neural tube closure. His::NT::C-CPE:: Cldn3EL2 that is designed to specifically target Cldn3 caused similar phenotypes. (a'-d') show immunofluorescence with anti-Cldn3 antibodies (green) or anti-ZO1 antibodies (red). Cldn3 was removed from the cell-cell junctions at the non-neural ectoderm of chick embryos after 5 h of treatment with C-CPE(200 µg/ml), C-CPE$^{LDR}$ (200 µg/ml), or His::NT::C-CPE::Cldn3EL2 (200 µg/ml).
Figure 11:
FIG. 11 shows the nucleotide and amino acid sequence of the His::NT::C-CPE::Cldn1EL2 polypeptide, in accordance with certain embodiments, which has been color-coded to differentiate the various domains as follows: His-tag is shown in blue; solubility tag is shown in purple; TEV recognition sequence is shown in orange; C-CPE region is shown in grey; and claudin EL2 domain is shown in green.
Figure 15:
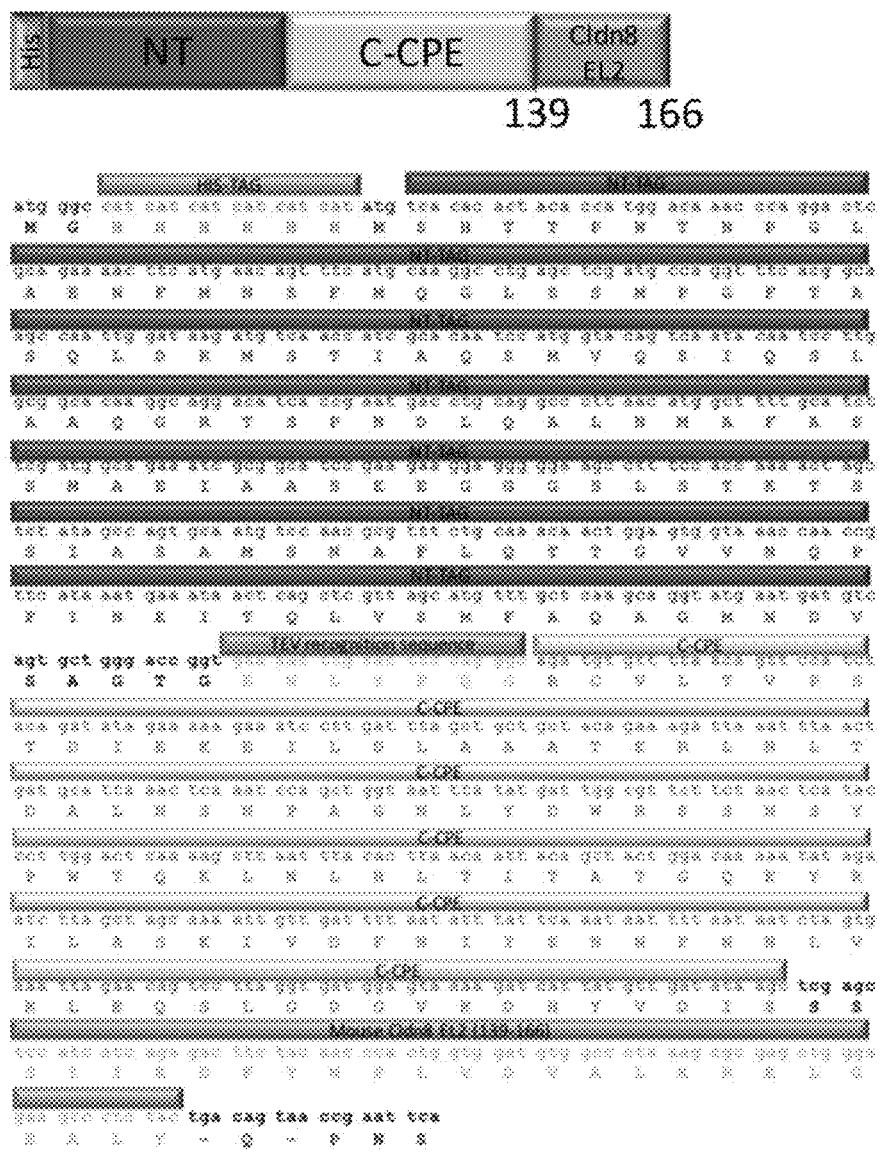
FIG. 15 shows the nucleotide and amino acid sequence of the His::NT::C-CPE::Cldn8EL2 polypeptide, in accordance with certain embodiments, which has been color-coded to differentiate the various domains as follows: His-tag is shown in blue; solubility tag is shown in purple; TEV recognition sequence is shown in orange; C-CPE region is shown in grey; and claudin EL2 domain is shown in green.

Finally, we switched to our final solubility tag, N-terminal domain from *Euprosthenops australis* major ampullate spidroin 1 (NT), which is derived from spider silk. This tag enabled us to purify high yields of our soluble Cldn11-targeting protein, hereafter referred to as His::NT::C-CPE:: Cldn11EL2 (FIG. 5; SEQ ID NO 6). The protein thus generated has four constitutive domains: (1) a purification tag; (2) a solubility tag; (3) the C-CPE excluding the claudin binding domain; and (4) the second extracellular loop (EL2) of Cldn11. The nucleotide and amino acid sequence of this His::NT::C-CPE::Cldn11EL2 polypeptide (SEQ ID NO: 6) is shown in FIG. 6.

Example 2. His::NT::C-CPE::Cldn11EL2 Disrupts the BTB and Increases SSC Engraftment After successfully generating His::NT::C-CPE::Cldn11EL2, we next tested the biological effects of His::NT::C-CPE::Cldn11EL2 on the BTB in mice. Our first step was to assess if His::NT::C-CPE::Cldn11EL2 was capable of reducing the expression of Cldn11 in the tight junctions of the BTB. Assuming that the His: :NT::C-CPE::Cldn11EL2 has kinetics similar to C-CPE, we began by injecting, into the seminiferous tubules of busulfan-treated male mice, either GST (control) or C-CPE plus His::NT::C-CPE::Cldn11EL2,and waited 3 days before performing immunofluorescence to assess expression of Cldn8 and Cldn11 (FIG. 7A). We observed that Cldn8 expression was reduced in the tight junctions of the BTB, as expected due to the presence of C-CPE, however Cldn11 expression appeared to be unaffected (FIG. 7B).

Based on this observation, we next employed an alternative approach to administer C-CPE and His::NT::C-CPE::Cldn11EL2, where Cldn11 was injected into the testis of busulfan-treated males 3 days after C-CPE injection and an additional 1 day was given before testis were collected and analyzed (FIG. 8A). Using this administration scheme, both Cldn8 and Cldn11 expression were reduced at the tight junctions of the BTB (FIG. 8B). These findings illustrate that His::NT::C-CPE::Cldn11EL2 was capable of reducing the expression of Cldn11 at the tight junctions, thereby disrupting the BTB, in vivo. Comparison of data from the injection strategy used in FIG. 7 versus FIG. 8 suggests that the effect of His::NT::C-CPE::Cldn11EL2 on Cldn11 was more transient than the effect of C-CPE on Cldn8.

Based on this finding that His::NT::C-CPE::Cldn11EL2 administration reduced expression of Cldn11 in the seminiferous tubule tight junctions and disrupted the BTB, we next assessed its ability to influence SSC transplantation efficiency. To evaluate this, we injected C-CPE at day 0, and at day 3 we injected His: :NT::C-CPE::Cldn11EL2 and $10^4$-$10^5$ donor testis cells from Rosa26-LacZ mice into seminiferous tubules of one testis of a C57BL/6×129F1 recipient mouse (FIG. 9A). After 2-month, testes were collected and assayed for transplanted SSC colonies. We observed a 3-4 fold increase in engrafted SSCs in the presence of C-CPE or His::NT::C-CPE::Cldn11EL2 alone relative to GST-controls, and a 5-fold increase in mice treated with C-CPE and His::NT::C-CPE::Cldn11EL2 in combination (FIG. 9B). These results demonstrated that administration of His::NT::C-CPE::Cldn11EL2 increased SSC engraftment in the testes. As successful transplantation of SSCs to the testes of infertile mice is known to restore fertility [30], we anticipate that administration of His::NT::C-CPE::Cldn11EL2 will also restore fertility in our mice and enable them to sire offspring.

Example 3. Selective Removal of Claudins from the Neural Tube Using Claudin-Targeting Polypeptides Neural tube defects (NTDs) occur with an incidence of ~1 per 1000 live births. They are grouped into three categories based on the location of the defect: anencephaly, when the neural tube remains open in the head region; spina bifida, when the opening is at the level of the spinal cord; and craniorachischisis, when the neural tube has failed to close along the entire anterior-posterior axis. Neural tube closure occurs during the third week of human development and between 24 (HH4) and 42 (HH11) hours in chick embryos. The process is the same in human and chick embryos.

Selective removal of claudins causes NTDs. We used the non-toxic C-terminal domain of *C. perfringens* enterotoxin (C-CPE) to selectively and simultaneously remove a subset of claudins from tight junctions during neural tube morphogenesis in chick embryos [Baumholtz, A. I. et al., (2017) Developmental Biology 428:25-38; PMID: 28545845]. C-CPE is ideal to target removal of claudins: (i) it is not cytotoxic to cells, (ii) it binds specifically to a limited subset of claudins (Cldn-3, -4, -6, -7, -8 and -14), causing their removal from tight junctions without affecting the localization of other family members, (iii) it does not affect gene expression so that upon C-CPE removal susceptible claudins can repopulate tight junctions, allowing transient disruption of tight junctions, and (iv) it does not bind to any other cell surface proteins. Thus, phenotypes resulting from C-CPE treatments are the direct result of its interactions with claudins.

Four C-CPE sensitive claudins are expressed in the ectoderm during neural tube closure [Collins, M. M., Baumholtz, A. I, and Ryan, A. K. (2013) Tissue Barriers. 1(3): e24517. Doi:10/4161/tisb.24517]. Cldn-3 is enriched in the non-neural ectoderm; Cldn-8 and -14 are enriched in the neural ectoderm; and Cldn-4 is expressed in both the neural and non-neural ectoderm. We observed that C-CPE selectively removed Cldn-3, -4, and -8, but not Cldn-14, from tight junctions within 5 h of treatment. The CPE-insensitive Cldn-1 and the cytoplasmic adaptor protein ZO-1 remained localized to the apical domain. All the embryos cultured in ≥200 μg/ml C-CPE had open NTDs (n=206) [Baumholtz et al., 2017 and FIG. 10*b*]. NTDs were not observed in embryos cultured in control GST media (FIG. 10*a*).

Claudin-3 is required for neural fold fusion (phase 4). We obtained a C-CPE variant that selectively binds and removes Cldn-3 (C-CPE$^{LDR}$, which is C-CPE with three point mutations in the claudin binding domain). Embryos incubated with C-CPE$^{LDR}$ were of normal length but had open NTDs that were consistent with a failure of neural fold fusion during the final phase of neural tube closure (FIG. 10*c*, 10*c*"). We confirmed that C-CPE$^{LDR}$ removed Cldn3 from tight junctions in the chick ectoderm (FIG. 10*c*').

In sum, as a proof-of-principle for biological activity of our claudin targeting polypeptide, we designed the His::NT: :C-CPE: :Cldn3EL2 polypeptide to target Cldn3. We predicted that if His::NT::C-CPE::Cldn3EL2 specifically targeted Cldn3, the chick embryos would have mild open neural tube defects similar to the ones observed following treatment with C-CPE$^{LDR}$. If we observed no phenotype, we would conclude that the peptide was not biologically active, and if we observed a more severe phenotype similar to that observed when we used C-CPE to deplete multiple claudin family members, we would conclude that the His::NT::C-CPE::Cldn3EL2 had broader claudin specificity and was not uniquely targeting Cldn3. The results show that, when chick embryos were treated with concentrations higher than 200 µg/ml, the embryos treated with His::NT::C-CPE::Cldn3EL2 replicated the phenotype seen by C-CPE$^{LDR}$, where the neural tube was able to elevate but the final steps of neural tube fusion were impaired (FIGS. 10c, 10d). His::NT::C-CPE::Cldn3EL2 was also confirmed to remove Cldn3 after 5h of treatment similar to C-CPE and C-CPE$^{LDR}$ (FIGS. 10a'-10d'). These data confirmed our hypothesis that His::NT::C-CPE::Cldn3EL2 can specifically target Cldn3 without affecting Cldn4 or -8, since a more severe phenotype was not observed.

REFERENCES

1. Chapman, R. M., Sutcliffe, S. B. and Malpas, J. S. (1979) Cytotoxic-induced ovarian failure in women with Hodgkin's disease. *JAMA* 242: 1877-1886.

2. Schilsky, R. L., Lewis, B. J., Sherins, R. J., and Young, R. C. (1980) Gonadal dysfunction in patients receiving chemotherapy for cancer. *Ann. Intern. Med.* 93: 109-114.

3. Liu S, Semenciw R, Mao Y. (2003) Increasing incidence of non-Hodgkin's lymphoma in Canada, 1970-1996: age-period-cohort analysis. *Hematol Oncol* 21: 57-66.

4. Richiardi L, Bellocco R, Adami H O, Torrang A, Barlow L, Hakulinen T, Rahu M, Stengrevics A, Storm H, Tretli S, Kurtinaitis J, Tyczynski J E, Akre O. Testicular cancer incidence in eight northern European countries: secular and recent trends. *Cancer Epidemiol Biomarkers Prev.* 2004; 13: 2157-2166.

5. Oatley J M, Brinster R L. Regulation of spermatogonial stem cell self-renewal in mammals. *Annu Rev Cell Dev Biol.* 2008;24:263-286.

6. Griswold M. D. (1995) Interactions between germ cells and Sertoli cells in the testis. *Biol. Reprod.* 52: 211-216.

7. Kierszenbaum, A. L. (1994) Mammalian spermatogenesis in vivo and in vitro: a partnership of spermatogenic and somatic cell lineages. *Endocrine Reviews* 15: 116-134.

8. Russell, L. D., Ettlin, R. A., Sinha Hikim, A. P., and Clegg, E. D. (1990) In: *Hitological and histopathological evaluation of the testis*. Cache River Press (Clearwater, USA), pp1-58.

9. Morrow C M, Mruk D, Cheng C Y, and Hess R A. (2010) Claudin and occludin expression and function in the seminiferous epithelium. *Philos Trans R Soc Lond B Biol Sci.* 365:1679-1696.

10. Nagano, M C. (2003). Homing efficiency and proliferation kinetics of male germ line stem cells following transplantation in mice. *Biol Reprod.* 69: 701-707.

11. Ebata, K. T., Zhang, X., and Nagano, M. C. (2007). Male germ line stem cells have an altered potential to proliferate and differentiate during postnatal development in mice. Biol Reprod. 76, 841-847.

12. Shinohara T, Orwig K E, Avarbock M R, and Brinster R L. (2001) Remodeling of the postnatal mouse testis is accompanied by dramatic changes in stem cell number and niche accessibility. *Proc Natl Acad Sci USA.* 98:6186-6191.

13. Mruk, D. D. and Cheng, C. Y. (2004) Sertoli-Sertoli and Sertoli-germ cell interactions and their significance in germ cell movement in the seminiferous epithelium during spermatogenesis. *Endocr. Rev.* 25:747-806.

14. Takashima S, Kanatsu-Shinohara M, Tanaka T, Takehashi M, Morimoto H, and Shinohara T. (2011) Rac mediates mouse spermatogonial stem cell homing to germline niches by regulating transmigration through the blood-testis barrier. *Cell Stem Cell.* 9:463-475.

15. Moroi S, Saitou M, Fujimoto K, Sakakibara A, Furuse M, Yoshida O, Tsukita S. (1998) Occludin is concentrated at tight junctions of mouse/rat but not human/guinea pig Sertoli cells in testes. *Am. J. Physiol.* 174: C1708-C1717.

16. Gupta, I. R; Ryan, A. K. (2010) Claudins: Unlocking the code to tight junction function during embryogenesis and in disease. *Clin. Genet.* 77, 314-325.

17. Krause, G., Winkler, L., Mueller, S. L., Haseloff, R. F., Piontek, J. and Blasig, I. E. (2008) Structure and function of claudins. *Biochim. Biophys. Acta* 1778:631-645.

18. Gow, A., Southwood, C. M., Li, J. S., Pariali, M., Riordan, G. P., Brodie, S. E., Danias, J., Bronstein, J. M., Kachar, B., and Lazzarini, R. A. (1999) CNS myelin and Sertoli cell tight junction strands are absent in Osp/claudin-11 null mice. *Cell* 99: 649-659.

19. Kanatsu-Shinohara M, Morimoto H, Watanabe S, and Shinohara T. (2018) Reversible inhibition of the blood-testis barrier protein improves stem cell homing in mouse testes. *J Reprod Develop.* 64:511-522.

20. Mitchell L A and Koval M. (2010) Specificity of interaction between *Clostridium perfringens* enterotoxin and claudin-family tight junction proteins. *Toxins (Basel).* 2:1595-1611.

21. Winkler L, Gehring C, Wenzel A, Müller S L, Piehl C, Krause G, Blasig I E, Piontek J. (2009) Molecular determinants of the interaction between *Clostridium perfringens* enterotoxin fragments and claudin-3. *J Biol Chem.* 284: 18863-18872.

22. Nagano M, Brinster C J, Orwig K E, Ryu B Y, Avarbock M R, Brinster R L. (2001) Transgenic mice produced by retroviral transduction of male germ-line stem cells. *Proc Natl Acad Sci USA.* 98:13090-13095.

23. Brinster R L and Avarbock M R (1994) Germline transmission of donor haplotype following spermatogonial transplantation. *Proc. Natl. Acad. Sci.* USA 91: 11303-11307.

24. Nagano M, Shinohara T, Avarbock M R, and Brinster R L. (2002) Retrovirus-mediated gene delivery into male germ line stem cells. *FEBS Lett.* 475:7-10.

25. Kubota H and Brinster RL (2006) Technology insight: In vitro culture of spermatogonial stem cells and their potential therapeutic uses. *Nat Clin Pract Endocrinol Metab.* 2:99-108

26. Fujita K, Katahira J, Horiguchi Y, Sonoda N, Furuse M, and Tsukita S. (2000) *Clostridium perfringens* enterotoxin binds to the second extracellular loop of claudin-3, a tight junction integral membrane protein. *FEBS Lett.* 476: 258-261.

27. Sonoda N, Furuse M, Sasaki H, Yonemura S, Katahira J, Horiguchi Y, and Tsukita S. (1999) *Clostridium perfringens* enterotoxin fragment removes specific claudins from tight junction strands: Evidence for direct involvement of claudins in tight junction barrier. *J Cell Biol* 147:195-204.

28. Baumholtz A, Simard A, Nikolopoulou, E, Osenburg M, Collins M M, Piontek A, Krause G, Pionek J, Greene N D E, and Ryan A K. (2017) Claudins are essential for cell shape changes and convergent extension movements during neural tube closure. *Dev Biol.* 428(1): 25-38.

29. Winkler L, Gehring C, Wenzel A, Müller S L, Piehl C, Krause G, Blasig I E, and Piontek J. (2009) Molecular determinants of the interaction between *Clostridium perfringens* enterotoxin fragments and claudin-3. *J Biol Chem.* 284:18863-18872.

30. Nagano M, Brinster C J, Orwig K E, Buom-Yong R, Avarbock M R, and Brinster R L. (2001) Transgenic mice produced by retroviral transduction of male germ-line stem cells. *PNAS.* 98: 13090-13095.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A polypeptide construct consisting of:
   a first region comprising a C-terminal domain of *Clostridium perfringens* enterotoxin (C-CPE) with the claudin-binding domain removed; and
   a second region comprising the second extracellular loop (EL2) of a claudin protein;
   wherein the polypeptide construct specifically targets one or more claudin protein in the blood-brain barrier, the intestinal barrier, the blood-testis barrier (BTB), or the kidney nephronic barrier and can transiently disrupt tight junctions therein.

2. The polypeptide construct according to claim 1, wherein the first region comprises amino acids 186 to 290 of *Clostridium perfringens* enterotoxin.

3. The polypeptide construct according to claim 1, wherein the first region comprises or consists of the amino acid sequence set forth in SEQ ID NO: 14.

4. The polypeptide construct according to claim 1, wherein the second region comprises the entire EL2 domain of a claudin.

5. The polypeptide construct according to claim 4, wherein the second region comprises or consists of the amino acid sequence set forth in any one of SEQ ID NOs: 7-12 and 15-40.

6. The polypeptide construct according to claim 1, wherein the second region comprises the EL2 of claudin 1, 2, 3, 4, 5, 6, 7, 8, 9, 10, 11, 12, 14, 15, 16 or 19.

7. The polypeptide construct according to claim 1, wherein the polypeptide construct is linked to one or more tag region.

8. The polypeptide construct according to claim 7, wherein the tag region is a detectable tag such as a His tag; a tag for purification such as a His tag or a GST tag; and/or a tag for increasing solubility of the polypeptide such as the N-terminal domain from *Euprosthenops australis* major ampullate spidroin 1 (NT).

9. The polypeptide construct according to claim 1, wherein the polypeptide construct is linked to a Tobacco Etch Virus (TEV) protease recognition sequence.

10. A polypeptide construct comprising or consisting of the sequence set forth in any one of SEQ ID Nos: 1-6.

11. A pharmaceutical composition comprising the polypeptide construct of claim 1 and a pharmaceutically acceptable carrier, diluent or excipient.

12. A pharmaceutical composition comprising the polypeptide construct of claim 10 and a pharmaceutically acceptable carrier, diluent or excipient.

* * * * *